United States Patent
Skelton et al.

(10) Patent No.: US 12,080,409 B2
(45) Date of Patent: Sep. 3, 2024

(54) SECURE SOFTWARE UPDATES AND ARCHITECTURES

(71) Applicant: Stryker Corporation, Kalamazoo, MI (US)

(72) Inventors: Dennis M. Skelton, Woodinville, WA (US); Steven Barry Duke, Bothell, WA (US); Richard Mackie, Bellevue, WA (US); Mark Rutzer, Seattle, WA (US); James Wootten, Kirkland, WA (US); Alexander Frolov, Bothell, WA (US); Mark G. Killebrew, San Clemente, CA (US); Seshadri K. Padmanabha, Redmond, WA (US); David B. Stewart, Carnation, WA (US); Robert Bales, Mountlake Terrace, WA (US); Dale R. Beuning, Seattle, WA (US)

(73) Assignee: Stryker Corporation, Kalamazoo, MI (US)

( * ) Notice: Subject to any disclaimer, the term of this patent is extended or adjusted under 35 U.S.C. 154(b) by 345 days.

(21) Appl. No.: 17/543,674

(22) Filed: Dec. 6, 2021

(65) Prior Publication Data

US 2022/0181012 A1    Jun. 9, 2022

Related U.S. Application Data

(60) Provisional application No. 63/122,337, filed on Dec. 7, 2020.

(51) Int. Cl.
*G06F 9/44* (2018.01)
*G06F 8/654* (2018.01)
*G06F 21/57* (2013.01)
*G16H 40/40* (2018.01)

(52) U.S. Cl.
CPC .............. *G16H 40/40* (2018.01); *G06F 8/654* (2018.02); *G06F 21/572* (2013.01); *G06F 2221/033* (2013.01)

(58) Field of Classification Search
None
See application file for complete search history.

(56) References Cited

U.S. PATENT DOCUMENTS

| | | | |
|---|---|---|---|
| 11,157,265 B2* | 10/2021 | Bulusu | G06F 9/4401 |
| 2012/0096451 A1* | 4/2012 | Tenbarge | G06F 11/1433 |
| | | | 717/170 |
| 2014/0277227 A1 | 9/2014 | Peterson et al. | |
| 2017/0024534 A1 | 1/2017 | Arrizza et al. | |

(Continued)

*Primary Examiner* — Qamrun Nahar
(74) *Attorney, Agent, or Firm* — Lee & Hayes, P.C.

(57) ABSTRACT

Systems and techniques to ensure reliable operation of devices, such as medical devices, that are configured to execute installed software are described. A secure software update process for the device utilizes multiple integrity checks in order to prove that software integrity has not been compromised before the device is allowed to be put into service with the software installed thereon. Also described is a computer architecture for an external defibrillator that isolates the execution of installed software applications by separately compiling the code for those applications and by executing the separately-compiled applications on different processors of the defibrillator. Among other things, this allows the defibrillator to be "brought online" faster, such as to deliver a shock to a patient.

20 Claims, 8 Drawing Sheets

(56) References Cited

U.S. PATENT DOCUMENTS

| | | | |
|---|---|---|---|
| 2017/0255779 A1* | 9/2017 | Caklovic | G06F 21/51 |
| 2018/0137285 A1* | 5/2018 | Yamada | G06F 21/575 |
| 2020/0221263 A1* | 7/2020 | Sturman | H04W 4/12 |
| 2021/0232693 A1* | 7/2021 | Leenstra | G06F 9/45558 |

* cited by examiner

SECURE SOFTWARE UPDATES AND ARCHITECTURES

CROSS-REFERENCE TO RELATED APPLICATION

This application claims the benefit of U.S. Provisional Application No. 63/122,337, titled "Secure Software Updates and Architectures" and filed on Dec. 7, 2020, and which is incorporated by reference herein in its entirety.

BACKGROUND

A defibrillator is a medical device configured to administer defibrillation therapy to a patient through electrodes. While service technicians possess the know-how and the security credentials to service a defibrillator, providing users of defibrillators with unfettered access to install their own software or hardware compromises the reliability of the defibrillator, which, in turn, may compromise the safety of a patient. Furthermore, in the process of servicing a defibrillator, there is a risk of downloading and installing malicious software—often called "malware"—which can be used to steal or destroy system resources, data, and private information, among other threats. Malware comes in many forms, such as computer viruses, worms, trojan horses, spyware, keystroke loggers, adware, and rootkits.

Furthermore, as advancements in defibrillator technology are continually being made, a greater number of software applications are typically installed on a defibrillator to provide enhanced functions and features. Some of these functions and features may be useful, but not critical to the core functionality of the defibrillator. The sheer amount of software and the way the software is architected on existing defibrillators may, at times, inhibit the defibrillator's ability to carry out this core functionality, or to otherwise meet requirements imposed by regulating bodies on such medical devices. The disclosure made herein is presented with respect to these and other considerations.

DETAILED DESCRIPTION

Figure 1:
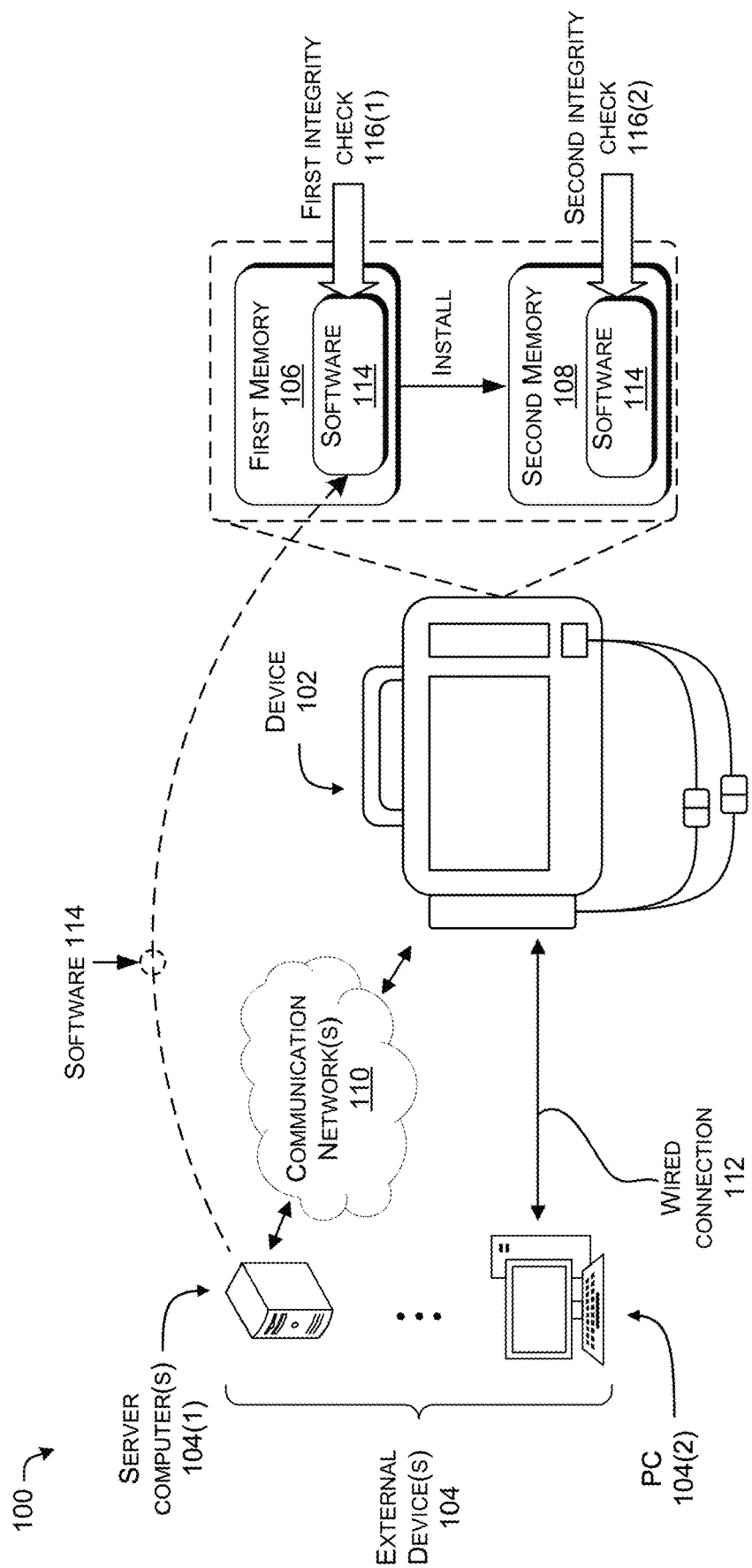
FIG. 1 illustrates an example system including a device that is in the process of updating software of the device.

The disclosure provides techniques and systems to ensure reliable operation of devices, such as medical devices, that are configured to execute installed software. Various implementations described herein relate to a device configured to perform multiple integrity checks on software—both before and after the software is installed on the device, as well as systems that include the device, and processes involving the device. According to some examples, the device is a medical device, such as a defibrillator (e.g., an external defibrillator). It is to be appreciated, however, that while the examples provided herein pertain to medical devices, the techniques described herein are equally applicable to other devices besides medical devices, such as vehicles that contain protected embedded software or firmware (e.g., airplanes, automobiles, smart appliances, traffic control, energy, consumer electronics, etc.), which benefit from a secure software update process that utilizes multiple integrity checks in order to prove that software integrity has not been compromised before the device is allowed to be put into service with the software installed thereon. According to some examples, the disclosed techniques to update software on a device enable the device to detect when hardware has been swapped (e.g., by detecting when a user has replaced a hardware component while the device was powered off). This prevents the installation of problematic (e.g., rogue) software on an equivalent hardware component, opening the device, swapping the legitimate hardware component for the equivalent hardware component having the problematic software, and bypassing the secure software update process. If a user were to swap hardware in this manner, the device can detect the hardware swap and may take remedial action, such as forcing a repeat of the secure software update process.

According to some examples, when a software update is initiated for a device, the device receives new software from an external device (e.g., a connected Personal Computer (PC), a server computer(s), the cloud, etc.) and stores the new software in first memory of the device as stored software. This phase of the software update process is sometimes referred to herein as a "download phase," although "download phase" is not meant to exclude a scenario where the stored software was received over a wired connection from an external device (e.g., a PC) that is collocated in an environment with the device or preloaded onto first memory during manufacturing before installing that memory onto the hardware circuit board. The first memory can also be what is normally considered a removable device (e.g., a Secure Digital high capacity (SDHC) card), if accessing that card requires opening the device to access it. According to some examples, the first memory in which the software is initially stored is used as a staging area to "hold" the stored software while a first integrity check is performed on the stored software. This is to avoid changing the currently installed software until it is known that the new software can meet the integrity checks. Aborting during download or during integrity checks leaves the device's previously-installed software in-tact. Furthermore, this is to ensure that the software's integrity has not been compromised, or that the device received the correct software, before the stored software is installed in second memory (e.g., electrically erasable programmable read-only memory (EEPROM), flash memory, NAND flash memory, other non-volatile memory, etc.) of the device. According to some examples, if, during the download phase, the stored software does not pass the first integrity check, the device refrains from installing the stored software in the second memory and the installation of the stored software is aborted. Even though the stored software did not pass the first integrity check, the device is still operable using the existing software that is currently installed in the second memory of the device. In this scenario, the device deletes the new software from the first memory, leaving the existing, installed software intact. In some examples, the device outputs a notification that the software update was unsuccessful, reports information indicating the same to a server computer(s), and reboots into a normal operating mode to execute the existing software.

In a scenario where the stored software passes the first integrity check, the software update proceeds to an "installation phase" where the stored software is installed in the second memory as installed software. Any existing software in the second memory is deleted from the second memory to make room for the new software. After installation of the new software in the second memory, the device performs a second integrity check on the installed software prior to enabling the device for use. In some example, this second integrity check is performed with external communication links of the device disabled, thus relying on the downloaded, digitally signed manifest file, which is now stored locally on the device. This mitigates the opportunity for external hacking while the checks are performed. The second integrity check also ensures that the integrity of the installed software has not been compromised prior to operating the device with the installed software, and it offers a layer of redundancy in checking the integrity of the software. If the installed software does not pass the second integrity check, the device, in some examples, is disabled so that it is at least temporarily unusable until a service technician restores the device's software. This disclosed software update process provides a highly-reliable device that is much more likely to operate as intended by the manufacturer or the vendor of the device. In examples where the device is a medical device (e.g., an external defibrillator), this also provides a device that is safe to use in association with a patient, such as to administer defibrillation therapy to the patient.

Also disclosed herein is a computer architecture for an external defibrillator that isolates the execution of a first software application—which is configured to control delivery of an electrical shock via a set of electrodes—from the execution of one or more second software applications—which is/are not involved in controlling delivery of the electrical shock to defibrillate a patient. The first software application is sometimes referred to herein as a "clinical application" that is used while the defibrillator is in a main mode of operation, sometimes referred to herein as the "patient mode." The second software application, in some examples, is a "setup application" that is used while the defibrillator is in a "setup mode." Another example of a second software application is an "install application" that is used while the defibrillator is in an "install mode" to install new software on the defibrillator. In some examples, the patient mode and the other modes (e.g., setup mode, install mode, etc.) are mutually exclusive from each other, meaning that the defibrillator does not operate in both modes simultaneously. In the setup mode, the user of the defibrillator is able to define customized settings for the defibrillator. The setup application and the install application are just two example types of second software applications, and it is to be appreciated that the second software application(s) can be any other type of application that is not involved in controlling delivery of the electrical shock to defibrillate a patient. The isolation of the execution of each software application is accomplished by compiling each software application separately from the other application. That is, the second software application (e.g., the setup application) is compiled separately from the first software application (e.g., the clinical application) in order to isolate the execution of the first software application on the defibrillator from execution of the second software application on the defibrillator.

According to some examples, these separately-compiled software applications are executed independently on a given processor of the defibrillator. In other words, two separately-compiled software applications may be prevented from executing on the same processor contemporaneously, which provides independence of the execution of a given software application that is executed by the processor. Among other things, isolating the execution of the clinical application from the setup application—e.g., through separately-compiled code—allows the defibrillator to be "brought online" quickly after the defibrillator is powered on (from a powered off state). The ability to ready the defibrillator quickly after powering on the defibrillator is due, at least in part, to the ability of a processor of the defibrillator to load the clinical application without having to load or execute the setup application before the defibrillator is fully ready to deliver a shock via the set of electrodes. This allows the defibrillator to load the first software application quickly in order to decrease the time it takes to treat a patient after the defibrillator is turned on. Additional technical benefits of the techniques and systems described herein are disclosed with reference to the following figures.

FIG. 1 illustrates an example system 100 including a device 102 that is receiving a software update from an external device 104. The device 102 shown in FIG. 1 is a defibrillator (e.g., an external defibrillator), but it is to be appreciated that, in other examples, the device 102 may represent a different type of medical device, such as a patient monitor, or a similar medical device. It is also to be appreciated that, in other examples, the device 102 may represent a non-medical device, such as a vehicle (e.g., an airplane, an automobile, etc.), or any other suitable device that benefits from a secure software update process that ensures that the correct software is received at the device, and that the integrity of the software installed on the device has not been compromised before the device is put into service using the software. For example, a self-driving car would benefit from the software update techniques described herein because proving that software integrity has not been compromised before executing the software in order to autonomously drive the car ensures that the car drives properly and that passengers on the road remain safe while the car is on the road. Nevertheless, the examples provided herein pertain to a device 102 that represents a medical device, and, specifically, a defibrillator, in order to illustrate the various features of the software update process and architectures described herein.

According to some examples, the device 102 includes memory, such as first memory 106, second memory 108, and possibly additional forms of memory. In an illustrative example, the first memory 106 represents first non-volatile memory, such as a Secure Digital (SD) card (e.g., a SDHC card, a micro SD (pSD) card), an embedded MultiMediaCard (eMMC), a hard drive, a USB memory, a serial peripheral interface (SPI) memory, a memory partition, or the like, and the second memory 108 represents second non-volatile memory, such as embedded flash memory, EEPROM, a hard disk drive (HDD), a solid-state drive (SDD), or the like. In some examples, the second memory 108 is a "non-removable" non-volatile memory, such as embedded flash memory that is soldered to a circuit board, and, hence, not easily removable, even when the housing of the device 102 is opened. According to some examples, the second memory 108 is configured to store the current version of the software that is executed to carry out the core functionality of the device 102. In an example of a defibrillator, the second memory 108 stores software that is loaded into working memory, such as random access memory (RAM) (not shown in FIG. 1), or a similar type of volatile memory, in order to execute the installed software in the working memory for purposes of administering defibrillation therapy to a patient by controlling the delivery of an electrical shock via electrodes of the defibrillator. Meanwhile, the first memory 106 is used as a staging area to "hold" software that is about to be installed in the second memory 108, assuming the software passes an integrity check to verify that the software has not been compromised. In some examples, the first memory 106 is used to retain verified, downloaded software corresponding to the currently installed software. This enables performing the second integrity check (described in more detail below) periodically (e.g., daily), as part of a periodic auto-test. In some examples, a quicker boot-time cyclic redundancy check (CRC) check can be performed on every boot-up of the device 102, and these CRCs can be checked periodically (e.g., daily) when doing the full integrity check.

As shown in FIG. 1, the device 102 is configured to communicate with external devices 104 over any suitable communication medium. For example, FIG. 1 shows the device 102 as communicating with a server computer(s) 104(1) over a computer network 110. According to some examples, the computer network 110 represents and/or includes the Internet, other types of data and/or voice networks, a wired infrastructure (e.g., coaxial cable, fiber optic cable, etc.), a wireless infrastructure (e.g., radio frequencies (RF), cellular, satellite, etc.), and/or other connection technologies. According to some examples, the server computer(s) 104(1) is part of a network-accessible computing platform that is maintained and accessible via the computer network 110. Network-accessible computing platforms such as this are sometimes referred to using terms such as "on-demand computing", "software as a service (SaaS)", "platform computing", "network-accessible platform", "cloud services", "data centers", and so forth. In general, the server computer(s) 104(1) is configured to collect data from devices, such as the device 102, and is configured to send data to devices, such as the device 102. FIG. 1 also depicts a PC 104(2) that is communicatively coupled to the device 102 over a wired connection 112. Accordingly, the device 102, in some examples, is equipped with one or more physical ports (e.g., an access port(s)) to facilitate the wired connection to a collocated external device 104 and/or to a communication network(s) 110. The device 102, in some examples, is also, or alternatively, equipped with one or more wireless communication interfaces (e.g., a radio(s)), such as a Bluetooth Low Energy (BLE) radio, a Wi-Fi radio, and/or a cellular radio, and so on.

In the example of FIG. 1, the device 102 is actively updating its software. It is to be appreciated that updating software occurs after initially installing software on the device 102 as part of an "initial software load" or an "initial software install." The initial software load can be performed as an initial step in manufacturing, after individual printed circuit board assemblies (PCBAs) have been assembled into a closed unit. The PCBAs may have been previously component-tested and thus include some software installed, and the manufacturer of the PCBA may have installed a bootloader onto each microcontroller. A software repair operation can be performed if the device 102 is in a state that prevents updating using the installation process described herein. The device 102 can end up in this state if either a bootloader fails, or there are hardware or software failures that prevent a successful write then verify of any flash segment. The initial software load and the software repair may both use the same method to perform a full and clean software install. In some examples, the software packages are updated and the logs are cleared. Items that may not be cleared can include EEPROMs that include lifetime counters and time monitors, calibration data (if present), and PCBA hardware version info. If a particular microcontroller bootloader is not installed, or not executing correctly, it can be repaired by opening the device 102, and either using JTAG to reprogram it, or swapping the PCBA to one that has an operable bootloader on it. Other software is to be loaded from the package being installed, without any reliance on the device 102 being previously operational. This makes the technique suitable for initial software load and for repairing fielded devices 102 that have corrupted software or compromised software configuration due to repair of the device 102.

A processor(s) of the device 102 may support a boot-mode feature to boot remotely over USB. This feature can be leveraged through an access port of the device 102, and a general purpose input/output (GPIO) controlled by a power management processor. A remote boot, sometimes referred to herein as an "unbrick boot", may involve having the power management processor of the device 102 activate that GPIO when it powers on the processor(s) of the device 102. This feature can be triggered in one of two ways. A first way is via a special access port cable. That is, the access port of the device 102 may have a pin (e.g., a MfgOnOff pin), that is floating and pulled up internally in the device 102. That produces a normal boot. If that pin is grounded through use of a special cable when AUX power is applied to the device 102 and no batteries are installed, the device 102 may perform the unbrick boot instead of normal boot. A second way is via a power key, with a regular access port cable. That is, with no power on the device 102 (no batteries and no AUX power), a user may press and hold a power key of the device 102. AUX power may be applied, and when a light emitting diode(s) (LEDs) of the device 102 light up, the user may release the power key. The transition of the power key from pressed to not pressed within a period of time (e.g., five seconds) of applying the AUX power may also trigger the unbrick boot. This technique can be used by service personnel for field repair of the device 102, and/or by developers and failure analysis. The BootROM of the processor(s) can then wait for the connected external device 104 (e.g., a personal computer (PC)) to deliver the QnxIPL and QnxAltOS (See detail below) directly into RAM of the device 102, and then issue a jump command to trigger QnxIPL. That in turn boots QnxAltOS. At this time, a connection (e.g., openssl connection) to the device 102 is available. The external device 104 is now able to execute commands on the device 102 to download software and initiate the install. The device's 102 integrity checks described herein may verify that the software loaded is a formally built package and not a developer package, in order to mark the device 102 as a locked production software.

Once the external device 104 is able to execute commands on the device 102, then the external device 104 can perform functions including, without limitation, (i) partitioning a micro SD card, and triggering the "reformat" on the device 102, which formats each partition and Qnx embedded transaction file system (ETFS) and erase the microcontroller applications, (ii) downloading the software package to the/etfs/staging/working folder on the device 102, and (iii) unzipping each package.

Once the software has been staged, then the device 102 is ready to execute the install script with a "clean" option. In some examples, a flag (e.g., an "install-in-progress" flag)

may be set so that if power is removed while software installation is in progress, the software install can be resumed, rather than attempting to boot software that might not yet be fully installed or verified. From this point forward, the install script may be executed with a forced clean install for every software component and subsequent reboots for install auto-test and a return to setup mode to report results.

Referring again to FIG. 1, the software update process is initiated automatically (e.g., on a periodic basis by checking in with an external device 104 for available software updates), and/or a user initiates the software update process. In the illustrated example, the device 102 receives, from the server computer(s) 104(1) over the communication network(s) 110, software 114 that is to be installed in the second memory 108, but the device 102 initially stores the software 114 in the first memory 106 as stored software 114. Said another way, the device 102 downloads the software 114 to the first memory 106 as downloaded software 114. The stored/downloaded software 114 is associated with a software update for the device 102, meaning that the software 114 provides enhanced features or functionality to the device 102, and/or the software 114 fixes a "bug" and/or a vulnerability in the existing software that is currently installed in the second memory 108 of the device 102. In an example, the software 114 represents a new version, or a latest version, of software from a manufacturer or a vendor of the device 102 that is to be executed on the device 102 during operation of the device 102. Thus, the device 102, at least in some instances, already has a current, but now outdated, version of software installed in the second memory 108 at the time when the software 114 is stored/downloaded to the first memory 106. This phase of the software update process is sometimes referred to herein as a "download phase." Although FIG. 1 depicts the software 114 being downloaded from a server computer(s) 104(1), the terminology "download phase" is not meant to exclude a scenario where the stored software 114 was received over a wired connection from an external device 104, such as the wired connection 112 from the PC 104(2), which may be collocated in an environment with the device 102.

The device 102 is configured to perform a first integrity check 116(1) on the stored/downloaded software 114. As will be described in more detail below, the first integrity check 116(1), in some examples, includes performing an integrity check on each file included in the software 114 (e.g., a software package), such as by computing a hash code (e.g., a Secure Hash Algorithm (SHA)-256 hash code and/or a digital signature) of the file and determining whether the computed hash code matches what is listed in a manifest file received from the external device 104, determining whether a part number and/or version number of the software (or a component of the software) matches the corresponding number specified in the manifest file, computing a cyclic redundancy check (CRC) for each image in the file and determining that the CRC matches the CRC listed in the corresponding version file for that image, etc. In this example, the integrity of the software is compromised if the computed hash code of the file does not match a corresponding code listed in the manifest file received from the external device 104, and/or if the part number and/or version number of the software (or a component of the software) does not match the corresponding number specified in the manifest file, and/or if the CRC for an image in one of the files does not match the CRC listed in the corresponding version file for that image. These are merely example ways of verifying the integrity of the stored/downloaded software 114, and other types of integrity checks can be performed during the first integrity check 116(1). If, after completing the download phase, the stored software 114 does not pass the first integrity check 116(1), the device 102 refrains from installing the stored software 114 in the second memory 108 and the installation of the stored software 114 is aborted. In this scenario, even though the stored software 114 did not pass the first integrity check 116(1) because it's integrity has been compromised, the device 102 is still operable using the existing software that is currently installed in the second memory 108 of the device 102, and the device 102 deletes the new software 114 from the WORKING folder of the first memory 106, leaving the existing, installed software in the second memory 108 intact, and the copy of the installed software still in the CURRENT folder of the first memory 106. In some examples, the device 102 outputs a notification that the software update was unsuccessful, reports information indicating the same to a server computer(s) 104(1), and reboots into a normal operating mode to execute the existing software.

FIG. 1 illustrates a scenario where the stored/downloaded software 114 passes the first integrity check 116(1), meaning that the integrity of the software 114 has not been compromised. Thus, based at least in part on the stored/downloaded software 114 having passed the first integrity check 116(1), the device 102 is configured to install the stored/downloaded software 114 in the second memory 108 of the device 102 as installed software 114. With the installed software 114 stored in the second memory 108, and prior to enabling the device 102 for use with the installed software 114, the device 102 is configured to perform a second integrity check 116(2) on the installed software 114.

The second integrity check 116(2), in some examples, is similar to the first integrity check 116(1) in that the second integrity check 116(2), for a second time, runs through each file included in the installed software 114 and compute a hash code (e.g., a SHA-256 hash code) of the file and determine whether the computed hash code matches what is listed in the manifest file received from the external device 104, determine whether a part number and/or version number of the software (or a component of the software) matches the corresponding number specified in the manifest file, compute a CRC for each image in the file and determining that the CRC matches the CRC listed in the corresponding version file for that image, etc. The second integrity check 116(2) may additionally compare the software that is stored in second memory 108 to the software that is stored in first memory 106, and re-perform the integrity tests on the software that is in first memory 106 to ensure that software hasn't been corrupted or maliciously altered. If the installed software 114 passes the second integrity check 116(2), the device 102 is enabled for use, and the device 102 is permitted to execute the installed software 114 in a mode of operation to carry out the core functionality of the device 102. In an example where the device 102 represents a medical device, such as a defibrillator, the medical device is enabled for use in association with a patient based at least in part on the installed software 114 having passed the second integrity check 116(2), such as by executing the installed software 114 in a patient mode to administer defibrillation therapy to a patient. That is, the installed software 114, in an illustrative example, includes, or represents, a clinical application that, when executed, controls delivery of an electrical shock via a set of electrodes to defibrillate a patient. If, on the other hand, the installed software 114 did not pass the second integrity check 116(2), the device 102 is disabled such that it is at least temporarily unusable (e.g., temporarily unusable in association with a patient). According to some examples, a notification is provided to a user of the device 102, such as by illuminating a service light on the device 102 indicating that the device 102 is in need of service from a service technician, displaying a similar message on a display of the device 102, and/or sending information to the server(s) computer 104(1) indicating that the software update was unsuccessful.

In this manner, by performing two sets of integrity checks 116—one to confirm what is downloaded into first memory 106 matches what is desired, and the other to confirm what is programmed into second memory 108 matches what is in first memory 106—on newly received software 114 before the software 114 is executed on the device 102 and the device 102 is put into use, the device 102 is trusted to operated reliably in the field. In the case of a medical device, this ensures that the safety of a patient receiving treatment from the medical device is preserved. In an illustrative example, the device 102 is configured to administer defibrillation therapy treatment via electrodes attached to a patient's chest. By checking the integrity of the software 114 at least once prior to installation, and once after installation, the device 102 operates reliably, thereby ensuring the safety of the patient who is receiving the defibrillation therapy. Further, the second integrity check 116(2) (which is similar to the first integrity check 116(1)) can be automatically re-performed on a periodic basis (e.g., daily) as part of a periodic (e.g., daily) auto-test (a separate application).

The two-memory approach described herein provides fault resilience against losing power during a software install. For example, once the install process begins, if the install process is interrupted, upon power-cycling the device 102, the software install can automatically retry. During a software retry, the integrity of the software 114 in the first memory 106 has already been checked, hardware swaps that may have occurred while the device 102 was without power can be detected, and the second integrity check 116(2) can be performed. This eliminates the window for "bricking" the device 102, which is when the device 102 is put into a state where software applications do not execute and software is unable to be installed on the device 102, and a user may be forced to send the device 102 to the manufacturer for repair.

The software install process is designed to be robust to loss of power, even if power is abruptly removed in the middle of a software install. If for any reason the software install fails, the software install can be retried if the microcontroller bootloaders and the QNX Initial Program Loader (IPL) and alternate OS (e.g., QnxAltOS) images are intact, by reapplying power; doing so is sometimes referred to herein as a "software installation retry" or "software retry". If QnxIPL or QnxAltOS is not installed correctly due to power loss while programming those, then the software repair technique can be used. If a microcontroller bootloader became corrupted, then the device 102 may be opened up, and either that bootloader may be reprogrammed (e.g., with Joint Test Action Group (JTAG)), or the relevant board may be replaced. To initiate a software installation retry, a user may remove the power sources (e.g., batteries and auxiliar (AUX)), reapply the battery and AUX power sources, and a processor of the device 102 dedicated to power management may reboot in response. When the power management processor reboots, the bootloader detects that a flag (e.g., an "Install-in-Progress" flag) is set, and reboots the device 102 into an install mode. This re-initiates the install script. The install script may skip renaming folders (See FIG. 3, below) if there is no staging area. This implies it is a software installation retry, as the staging area has already been renamed to current. The install script may traverse through each item for a second time, and the items previously programmed can be skipped with a verify. Then programming of items resumes with the first item that is not the correct version or not verified correctly.

Figure 2:
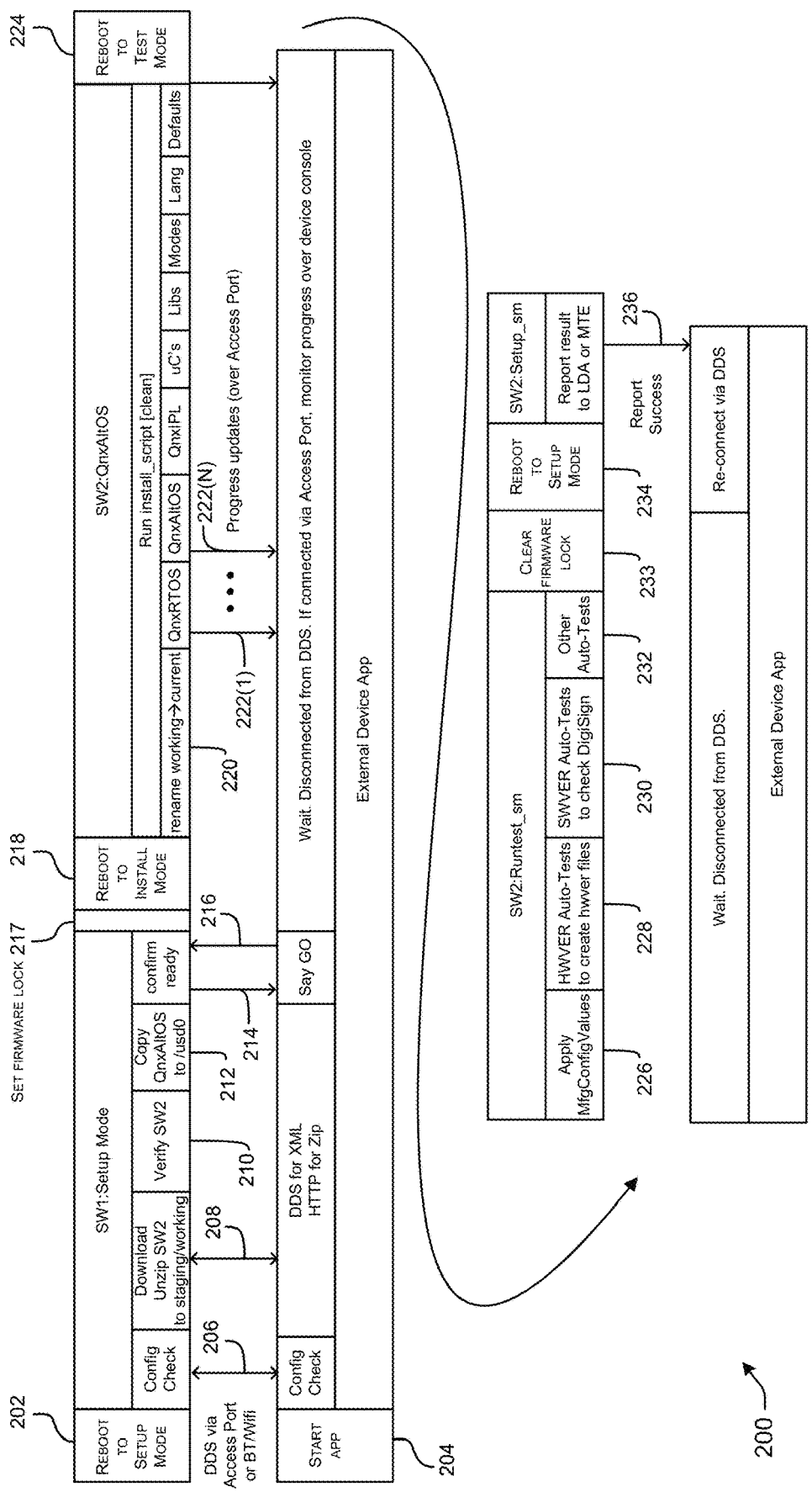
FIG. 2 illustrates a schematic diagram of an example software update process.

FIG. 2 illustrates a schematic diagram 200 of an example software update process. Although FIG. 2 illustrates steps in a particular order, implementations are not limited to the specific order of operations illustrated in FIG. 2. At 202, the device 102 reboots into a setup mode as part of initiating a software update for the device 102. The setup mode is an exemplary name of a mode in which the device 102 operates to download software and perform the first integrity check 116(1), as described herein, which is a different mode than a mode in which the device 102 operates to carry out the core functionality of the device 102, such as a patient mode for administering defibrillation therapy to a patient. At 204, an external device 104 starts executing an application (abbreviated to "app" in FIG. 2), to facilitate the software update for the device 102. The external device 104 possesses the new software 114 that is to be installed on the device 102. In FIG. 2, the new software 114 that is to be installed on the device 102 is referred to as "SW2". The existing software that is currently installed on the device 102 at the time of initiating the software update is referred to as "SW1". As described above with reference to FIG. 1, the device 102 and the external device 104 are communicatively connected via any suitable communication medium, such as a communication network(s) 110. In the example of FIG. 2, the device 102 and the external device 104 use a suitable communication protocol for real-time data exchange during the software update process, and the external device 104 is communicatively connected to the device 102 via a communications interface(s) of the device 102, such as via a physical access port over a wired connection 112, or via Bluetooth and/or WiFi radio(s) over a wireless connection.

To initiate the software update process, the device 102 boots into setup mode at 202, and the device 102 executes an existing setup application (SW1: Setup Mode) to perform various operations. According to some examples, the external device 104 and the device 102 exchange the current and desired software configuration for the device's 102 hardware configuration at 206 to determine if an update is needed. This force configuration check instruction designates the device 102 as the communication master between the two devices 102, 104, and the device 102 provides the external device 104 with information about the current configuration of the device 102 and the status of the device. Through this communications dialog (denoted by 206 in FIG. 2), the device 102 determines if a software update is needed, and the device 102 requests a software update by initiating a downloader state machine within setup mode. In an example, the device 102 sends information to the external device 104, the information identifying the existing software (SW1) that is currently installed on the device 102, and possibly the existing hardware components that are currently installed in the device 102, and the external device 104 returns information to the device 102 regarding a software update, if available.

At 208, the device 102 receives the new software 114 (SW2) from the external device 104 and stores the software 114 in the first memory 106 as stored software. Said another way, the device 102 downloads the software 114 (SW2) to the first memory 106 of the device 102 as downloaded software. As indicated in the example of FIG. 2, the device 102 uses a suitable communications protocol for downloading Extensible Markup Language (XML) objects (e.g., documents), and Hypertext Transfer Protocol (HTTP) for downloading ZIP files. At 208, in some examples, the device 102 unzips the software 114 packages it receives and stores the unzipped software 114 files in the first memory 106. As noted above, the first memory 106 represents first non-volatile memory, such as a SD card (e.g., μSD card). The first memory 106 is used during the download phase of the software update as a staging area to "hold" the software 114 in a working folder (the folders of the staging area are described in more detail with reference to FIG. 3).

At 210, the device 102 verifies the stored/downloaded software 114 (SW2) by performing the first integrity check 116(1). According to some examples, the first integrity check 116(1) performed at 210 uses SHA-256 and digital signatures to verify the integrity and the origin of the stored/downloaded software 114 (SW2). In an example, at 208, the device 102 downloads a manifest file, and at 210, the device 102 determines whether each file in the staging area of the first memory 106 matches the details in the manifest file. In this example, any discrepancy is flagged as an error and prevents a successful verification of the stored/downloaded software 114 (SW2) in the staging area of the first memory 106. In an illustrative example, the device 102 executes the following checks for each file of the stored/downloaded software 114 in the staging area of the first memory 106: (i) the computed SHA-256 hash code of the file matches what is listed in the manifest file; (ii) the software component's part number and software version number (which is integrated in a version file) matches the version number specified in the manifest file; and (iii) the CRC for each image in the file matches the CRC listed in the corresponding version file for that image. As each file succeeds in the verification at 210 (e.g., as each file passes the first integrity check 116(1)), one or more parameters for the file, such as the software identifier (ID), file name, and/or SHA-256 are added to a catalog and/or the manifest file. In a scenario where every file passes the first integrity check 116(1) at 210, the catalog then includes a full list of files that the device 102 is able to read during installation.

In some scenarios, the verification at 210 fails, meaning that the stored/downloaded software 114 (e.g., an individual file) did not pass the first integrity check 116(1). The root cause of the verification failure can vary, and may include process issues, hardware issues, and/or software issues, such as software received from an untrusted source. An untrusted source might be a malicious source attempting a cybersecurity attack. Regardless of the reason for a verification failure at 210, the device 102 nevertheless remains operational due to the existing software (SW1) remaining intact and installed in the second memory 106. In other words, installation of the stored/downloaded software 114 (SW2) was not initiated prior to the completion of the first integrity check 116(1), so the device 102 is able to operate using the existing software (SW1). In this verification failure scenario, and according to some examples, the device 102 sends information to the external device 104 indicating that the software update was unsuccessful.

FIG. 2, like FIG. 1, depicts a scenario where the stored/downloaded software 114 successfully passed the first integrity check 116(1). The installation phase of the software update is triggered if the verification at 210 passes for each file of the stored/downloaded software 114 package. According to some examples, an install application of the device 102 is included as part of an alternate operating system (OS) (e.g., safe mode in a Windows® OS), which is a minimalistic version of the OS that includes tools for installing software. The alternate OS with such install tools may allow for omitting the same install tools from the main OS, thereby preventing any accidental or intentional invocation of installation software when another program is running on the device 102. In the example of FIG. 2, the device 102 uses a QNX operating system, which is a Unix-like real-time operating system, to install the stored/downloaded software 114 (SW2) using one or more install scripts. Accordingly, the device 102 is configured to reboot and jump to this alternative OS image to perform installation of the stored/downloaded software 114. An "OS image" is a collection of reference files and folders usable to install and configure on operating system on a computing device, such as the device 102. To enable booting into this OS image, a copy of the OS image is stored in a location of the first memory 106 that is bootable by a QNX Initial Program Loader (IPL). In an example, the device 102 configures /usd0 in the first memory 106 (e.g., a μSD card) as an alternate boot location. Thus, at 212, and when the verification of the stored/downloaded software 114 (SW2) is complete and has passed the first integrity check 116(1) at 210, the device 102 copies the alternate OS image (e.g., QnxAltOS) from the working folder in the staging area of the first memory 106 to the μSD boot partition (e.g., /usd0) in the first memory 106.

In some examples, prior to transitioning to the installation phase of the software update, the device 102 sends the external device 104 a request to proceed at 214 (e.g., by confirming that it is ready for installation), and the device 102 receives, from the external device 104, a confirmation of the request to proceed at 216, which triggers the installation phase of the software update on the device 102. At 217, prior to rebooting into install mode, the device 102 may set an "install lock" into the firmware to disable the device 102 from performing tasks other than completing an install of the software 114. The firmware lock is to be cleared after verification of a successful install. At 218, and in response to the confirmation received from the external device 104 at 216, the device 102 reboots into an install mode to install the stored/downloaded software 114 (SW2) in the second memory 108. The install mode is an exemplary name of a mode in which the device 102 executes a separate application to install software from first memory 106 to second memory 108.

After rebooting into install mode and jumping to the copy of the alternate OS image (e.g., QnxAltOS), the device 102, at 220, in some examples, renames the folders in the staging area of the first memory 106 that are used to organize the data pertaining to the stored/downloaded software 114 (SW2). These folders are discussed in more detail below with reference to FIG. 3. In brief, a "working" folder that contains the stored/downloaded software 114 (SW2) is renamed to a "current" folder to reflect the software 114 that is about to be installed in the second memory 108 and become the currently-installed software of the device 102. One reason for doing this is to save the original verified downloaded files to enable performing periodic (e.g., daily) integrity checks of the software. Installation proceeds with steps of an install script. Installation is successful when all installed binaries match, and are verified to be, what is in the folder that was just renamed to the "current" folder (which contains the stored/downloaded software 114 (SW2)). According to some examples, the device 102 compares the binaries in the "current" folder of the staging area with what is already installed in the second memory 108, and if there is a match, the device 102 refrains from overwriting the matching binary in the second memory 108 during installation. This comparison can be performed with external communications links disconnected for added security, and/or subsequent comparisons can be performed on a periodic (e.g., daily) basis after the device 102 is put into service. In other examples, the device 102 overwrites all of the existing software (SW1) with the binaries of the stored/downloaded software 114 (SW2) as part of a clean/fresh install.

FIG. 2 illustrates example steps that are performed when running the install script, such as installing a QNX Real-time Operating System (RTOS), installing a QnxAltOS, installing a QnxIPL, installing microcontroller (μC) bootloaders, installing libraries, installing application code for software modes, installing language files, and installing defaults, but these are exemplary and other steps may be performed during the installation phase, depending on the package decomposition architected for the product software. Periodically, or in response to events, and if the external device 104 is connected over one way (e.g., an output-only) wired connection 112 to the device 102 via an access port(s) of the device 102, the device 102 provides progress updates 222(1) to 222(N) (N being any suitable integer) to the external device 104 so that the external device 104 is able to monitor the progress of the installation over a device console. The progress updates 222, in some examples, are used in troubleshooting or diagnostics if something an issue arises during installation.

Upon completion of the installation of the software 114 in the second memory 108 as installed software 114, the device 102 is configured to reboot into a test mode at 224. The device 102 is configured to perform one or more Auto-Tests while in test mode. According to some examples, the device 102 is also configured to perform the second integrity check 116(2) while in the test mode, and then periodically (e.g., daily) thereafter. At 226, manufacturing configuration values (MfgConfigValues) are applied so that they are accessible during the forthcoming Auto-Test(s). At 228, information identifying the hardware components that are currently installed in the device 102 is recorded to reflect the "state of hardware at last full install." Subsequent execution of a hardware version (HWVER) Auto-test is performed to detect hardware changes that might have occurred while the device 102 was powered off. An example process for detecting hardware swapping is described with reference to FIG. 6, below. In brief, if the device 102 is power-cycled (e.g., powered off and subsequently powered-on), the information recorded at 228 is usable to detect whether a hardware component of the device 102 has been replaced with a different hardware component, and, if so, the device 102 is disabled so that the device 102 is at least temporarily unusable (e.g., temporarily unusable in association with a patient, if the device 102 represents a medical device). In an example where the device 102 represents a defibrillator, example hardware components include a printed circuit board assembly (PCBA) that include a processor and memory on which the aforementioned software is loaded, among other components. If the PCBA or the components included on the PCBA were swapped by a user while the defibrillator was powered off, the information recorded at 228 is usable to detect this replacement of hardware. By detecting such a hardware-component swap, invalid, corrupted, and/or malicious software is prevented from entering the device 102 by changing the hardware with such malware pre-loaded.

At 230, a software version (SWVER) Auto-Test is performed to check a digital signature as part of the second integrity check 116(2). For example, a version file(s) is/are copied from the installed software 114 (SW2) during installation of the software 114, and this version file(s) include(s) a module name, version numbers, CRCs, SHA-256, a digital signature(s), and/or any other information that is usable to verify the integrity of the installed software 114 (SW2) and to ensure traceability back to the source code and build environment of the software. According to some examples, the second integrity check 116(2) verifies that the installed software 114 (SW2) still matches the information in the version file(s), and that the version file(s) still match(es) what is in the current folder of the staging area in the first memory 106. Any verification failure during this second integrity check 116(2) produces a version inconsistency service code and the device 102 is disabled based at least in part on the installed software 114 (SW2) having not passed the second integrity check 116(2).

At 232, other Auto-Tests are performed, in some examples. If the Auto-Tests performed at 228, 230, and 232, including the second integrity check 116(2), pass, the device 102 is ready to be placed into service. In some examples, a service light that was illuminated on the device 102 during the software update is turned off upon passing the Auto-Tests.

At 233, the firmware lock that was previously set at 217 is cleared if the Auto-Tests performed at 228, 230, including the second integrity check 116(2), pass, and regardless of a pass or a fail at 232. If the Auto-Tests performed at 228, 230 fail, the firmware lock remains set, as this scenario represents a failed attempt to securely install software, and recovery may occur by re-performing an Initial Software Install.

At 234, the device 102 reboots into the setup mode with a flag set in order to inform the device 102 that it is to complete the software update by connecting to the external device 104 and by sending information to the external device 104 indicating that the software update was successful. The installation restores default setup options. If the user specified a set of options that are different from the default, the user-specified options are applied automatically upon entry into the setup mode, before the device 102 sends information to the external device 104 indicating that the software update was successful. However, even if application of the setup options fails, the software update was still successful because the device 102 is capable of performing relevant functions with the default setup options.

Figure 3:
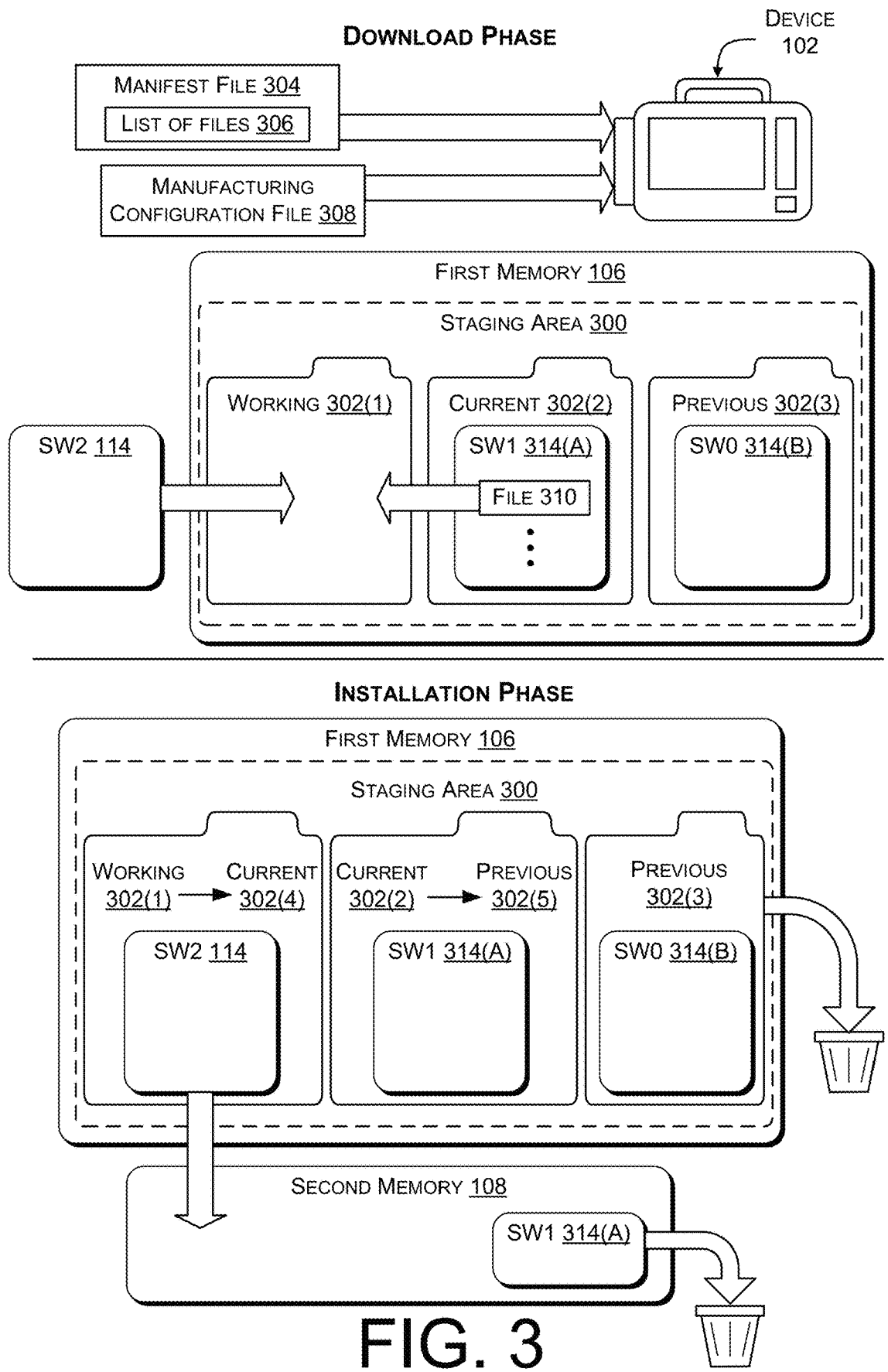
FIG. 3 illustrates an example technique for organizing data within a staging area of first memory of the device during a software update.

FIG. 3 illustrates an example technique for organizing data within a staging area of the first memory 106 of the device 102 during a software update. According to some examples, the first memory 106 of the device 102 organizes data within a staging area 300 that includes multiple folders 302. The example of FIG. 3 depicts three folders 302 in the staging area 300: a working folder 302(1), a current folder 302(2), and a previous folder 302(3). When a software update begins, the device 102 initiates the download phase, and the contents of the folders 302 are as follows: the current folder 302(2) contains a copy of the existing software (SW1) 314(A) that is currently installed in the second memory 108 of the device 102, the previous folder 302(3) contains a copy of the software (SW0) 314(B) that was previously installed on the device 102 prior to the installation of the existing software (SW1) 314(A), and the new software (SW2) 114 received from the external device 104 is populated within the working folder 302(1). The previous folder 302(3) can be used for diagnostics, in case something goes wrong with the software update and troubleshooting is performed. In this sense, it is to be appreciated that the previous folder 302(3) is optional and that the secure software update can be performed without the previous folder 302(3).

In some examples, in order to conserve resources (e.g., networking resources, power resources, memory resources, processing resources, etc.) when a partial software update occurs (some files are being updated, but not all), the device 102 refrains from requesting to download portions (e.g., files) of the software (SW2) 114 package that are already installed on the device 102, and that is/are therefore not going to change as a result of the software update. Accordingly, the device 102 is configured to determine which files are not going to change during a software update, and to store a copy(ies) of that/those file(s) in the working folder 302(1) instead of downloading that/those file(s) from the external device 104. Assuming the integrity of that/those file(s) has not been compromised, downloading that/those file(s) again is a wasteful exercise. Instead, those files are copied from the current folder 302(2) to the working folder 302(1) so that the working folder 302(1) contains a complete set once the downloads or copies are complete. Accordingly, a partial software update can be completed quicker by copying the file(s) that are available on the device 102 instead of downloading them.

The device 102, in some examples, uses a manifest file 304 that describes a complete valid configuration to determine what file(s) is/are not going to change during the software update so that the device 102 is able to refrain from downloading that/those file(s) from the external device 104. A manifest file, as used herein, is a file describing corresponding content as well as one or more elements thereof. The manifest file 304 is digitally signed with a digital signature for security purposes. In an example, during the download phase of the software update (as depicted at the top of FIG. 3), the device 102 receives a manifest file 304 from an external device 104. According to some examples, the manifest file 304 specifies a list of files 306 that are included in the software 114 associated with the software update, and the manifest file 304 may include a hash code (e.g., a SHA-256 hash code) for each file in the list of files 306. Notably, the files in the list of files 306 may not be digitally signed on an individual basis, as the digital signature of the manifest file 304 is sufficient to improve efficiency by shortening the time to perform the integrity checks described herein. In some examples, the manifest file 304 specifies a configuration of the software 114 to be installed on the device 102. In some examples, the device 102 also receives a manufacturing configuration file 308 that specifies the serial number of the device 102 and the hardware configuration of the device 102. The device 102 compares the serial number in the manufacturing configuration file 308 to the current serial number of the device 102 (which, in some examples, is hard-coded in memory of the device 102), and if the serial numbers match, the software update continues. If the serial numbers do not match, the installation of the software 114 is aborted.

Assuming that the serial numbers match, the device 102 analyzes the list of files 306 in the manifest file 304 to determine if any files are already installed on the device 102. The list of files 306 includes every software package that is to be installed. For each line item in the list of files 306, the device 102 determines if the line item (e.g., file) matches a file that is currently installed on the device 102. If a matching file 310 is found, the device 102 stores a copy of the file 310 in the working folder 302(1), and re-verifies the integrity of the file 310 by performing a preliminary integrity check on the copy of the file 310. For any line item (e.g., file) that either does not match what is installed on the device 102 or does not pass the preliminary integrity check, the device 102 requests to download that line item (e.g., file) from the external device 104. Accordingly, in some instances, the new software (SW2) 114 downloaded to the device 102 excludes one or more files, such as the file 310 if the file 310 matches a file listed in the manifest file 304 and if the file 310 passes the preliminary integrity check. Refraining from downloading files that are already installed on the device 102 allows for completing a software update process faster, as described herein. In some examples, the manifest file 304 may include a clean/fresh flag, which causes the device 102 to download and install every file without comparing the files to the previous version of the software.

According to some examples, the device 102 downloads the new software (SW2) 114 incrementally by populating the working folder 302(1) with the new software (SW2) piece-by-piece (e.g., file-by-file, package-by-package, etc.). Once the download of the new software (SW2) 114 to the first memory 106 is complete, and after copying and re-verifying any files that are not going to change during the software update and hence were not downloaded with the remaining software (SW2) 114, the working folder 302(1) contains the complete set of files in the new software 114 package, which is to be installed after performing the first integrity check 116(1) and validating/verifying the new software 114 to ensure that the integrity of any file(s) in the new software 114 has not been compromised. The first integrity check 116(1), as described herein, is performed on the stored/downloaded software 114 while the software 114 is contained within the working folder 302(1) within the staging area 300 of the first memory 106. It is to be appreciated that even if copied files, such as the file 310, pass the preliminary integrity check prior to downloading the remainder of the new software 114 package, those files, such as the file 310, are checked again for integrity as part of the first integrity check 116(1). This guards against a scenario where the file 310 has become corrupted after performance of the preliminary integrity check and prior to performance of the first integrity check 116(1). If the stored/downloaded software 114 contained in the working folder 302(1) passes the first integrity check 116(1), the software update transitions from the download phase to the installation phase, which is depicted at the bottom of FIG. 3.

During the installation phase of the software update, the device 102 renames the working folder 302(1) and the current folder 302(2), and the device 102 deletes the previous folder 302(3) from the staging area 300 of the first memory 106. After deleting the previous folder 302(3), for example, the current folder 302(2) is renamed to a new previous folder 302(5), and the working folder 302(1) is renamed to a new current folder 302(4). The new current folder 302(4) contains the software (SW2) 114 that is being installed. Therefore, after installation of the software (SW2) 114, the new current folder 302(4) will reflect the desired state of the installed software of the device 102. Meanwhile, the new previous folder 302(5) contains the existing software (SW1) 314(A) that, after installation of the new software (SW2) 114, will become a copy of the software (SW1) 314(A) that was previously installed on the device 102 prior to the installation of the new software (SW2) 114. The staging area 300 is now ready for the next time a software update is performed, and the second memory 108 stores the installed software (SW2) 114, and SW1 314(A) is deleted from the second memory 108, as it is now obsolete.

FIGS. 4-7 illustrate example processes related to various implementations of the present disclosure. Although FIGS. 4-7 illustrate separate processes, in various examples, a single entity can perform any combination of the processes. Furthermore, although each of FIGS. 4-7 illustrates steps in a particular order, implementations are not limited to the specific order of operations illustrated in the figures.

Figure 4:
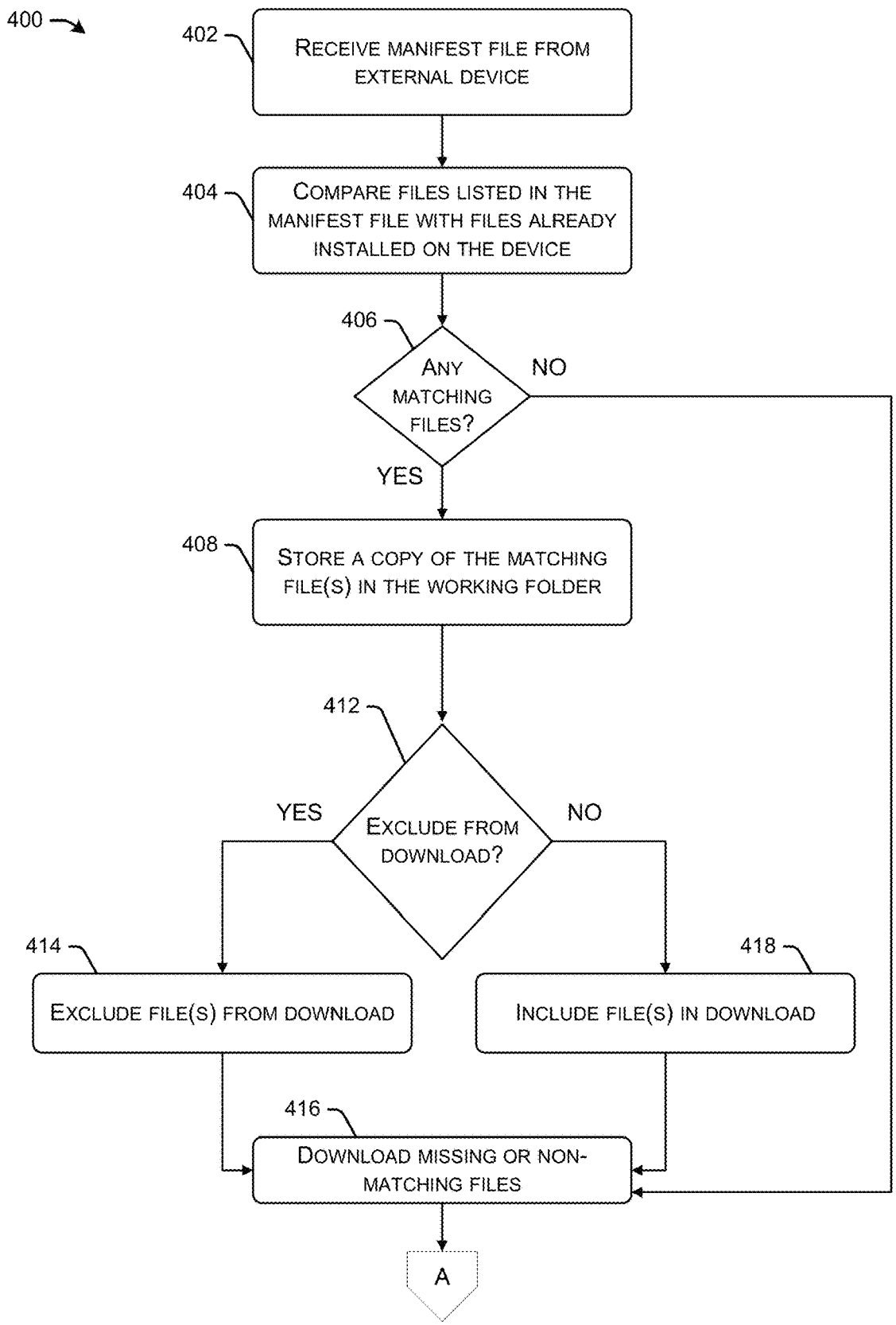
FIG. 4 illustrates an example process for determining software to download during a software update.

FIG. 4 illustrates an example process 400 for determining software to download during a software update. In various implementations, the process 400 is performed by an entity such as the device 102 (e.g., a processor(s) of the device 102).

At 402, the device 102 receives a manifest file 304 from an external device 104 (e.g., a server computer 104(1)). In some examples, the manifest file 304 specifies a list of files 306 included in the software 114 associated with a software update. Because the device 102 is usable in various locations, users who speak different languages may use the device 102. In order to provide software for the language(s) spoken by a user(s) of the device 102, the manifest file 304, in some examples, includes multiple listings of new software for each language that is available. In some examples, the manifest file 304 includes original equipment manufacturer (OEM) software packages.

At 404, the device 102 (e.g., a processor(s) of the device 102) compare files listed in the list of files 306 from the manifest file 304 with files included in the existing software (SW1) 314(A) that is currently installed on the device 102. In an example, a current folder 302(2) within the staging area 300 of the first memory 106 of the device 102 contains a copy of the existing software (SW1) 314(A), and the device 102 uses the copy of the existing software (SW1) 314(A) contained in the current folder 302(2) to perform the file comparison at 404.

At 406, the device 102 (e.g., a processor(s) of the device 102) determines whether there are any matching files based on the file comparison at 404. If, at 406, the device 102 determines that a first file in the list of files 306 matches a second file 310 of the copy of the existing software (SW1) 314(A) in the current folder 302(2), the process 400 follows the YES route from 406 to 408, where the device (e.g., a processor(s) of the device 102) stores a copy of the second file 310 in the working folder 302(1) within the staging area 300 of the first memory 106. In an example, this is performed for any number of matching files.

In some examples, the device 102 (e.g., a processor(s) of the device 102) analyzes the copy of the second file 310 (and any additional matching files). In an example, such analysis includes computing a hash code (e.g., a SHA-256 hash code) of the second file 310 and determining whether the computed hash code matches what is listed in the digitally-signed manifest file 304 received from the external device 104, determining whether a part number and/or version number associated with the second file 310 matches the corresponding number specified in the manifest file 304, computing a CRC for each image in the second file 310 and determining that the CRC matches the CRC listed in the corresponding version file for that image, etc. In an example, this is performed for any number of matching files.

At 412, the device 102 (e.g., a processor(s) of the device 102) determines whether to exclude any files from a request to download the new software (SW2) 114. For example, based on analyzing the copy of the second file 310 (and any additional matching files), the device 102 (e.g., a processor(s) of the device 102) may determine that it already possesses a valid file(s). In this scenario, the process 400 follows the YES route from 412 to 414, where the device 102 (e.g., a processor(s) of the device 102) excludes a file(s) (e.g., the first file that matched the second file 310) from a request to download the new software (SW2) 114. This is because doing so would be wasteful, since the device 102 already possesses the file(s) (i.e., the second file 310).

At 416, the device 102 downloads the software (SW2) 114 to the working folder 302(1) from the external device 104.

Following 414, the software (SW2) 114 downloaded at 416 excludes the first file (and any additional files) that the device 102 already possesses and that passed the preliminary integrity check. Accordingly, the file(s) downloaded at 416 may represent missing or non-matching files.

If, at 412, the device 102 (e.g., a processor(s) of the device 102) determines that the copy of the second file 310 did not pass the preliminary integrity check, the process 400 follows the NO route from 412 to 418 where the device 102 (e.g., a processor(s) of the device 102) includes the first file in the request to download the software, and, at 416, the device 102 downloads the software (SW2) 114 including the first file. The first file is included in the download at 416 because, even though the device 102 possesses the same file (i.e., the second file 310), the second file 310 did not pass the preliminary integrity check, so its integrity has been compromised and the device 102 downloads a new version of that file at 416.

Referring again to block 406, if the device 102 (e.g., a processor(s) of the device 102) determines that there are no matching files based on the file comparison at 404, which generally occurs when there is a full software update rather than a partial software update, the process 400 follows the NO route from 406 to 416 where the device 102 downloads the software (SW2) 114. In this scenario, because the device 102 does not possess any of the files in the new software (SW2) 114 package, the entire software (SW2) 114 package is downloaded at 416.

Accordingly, in one example implementation of the process 400, before a device 102 downloads new software (e.g., the software 114), the device 102 determines what part of the new software 114 it already has installed, and the device 102 puts a copy of that part of the new software 114 in a testing area of the device 102 to make sure it is still good software and to prevent corrupting the already-installed software, and if the copied part of the new software 114 is still good software, the device 102 doesn't bother downloading that part of the new software, and the device 102 downloads the remainder of the new software 114 without downloading the "still good software."

Figure 5:
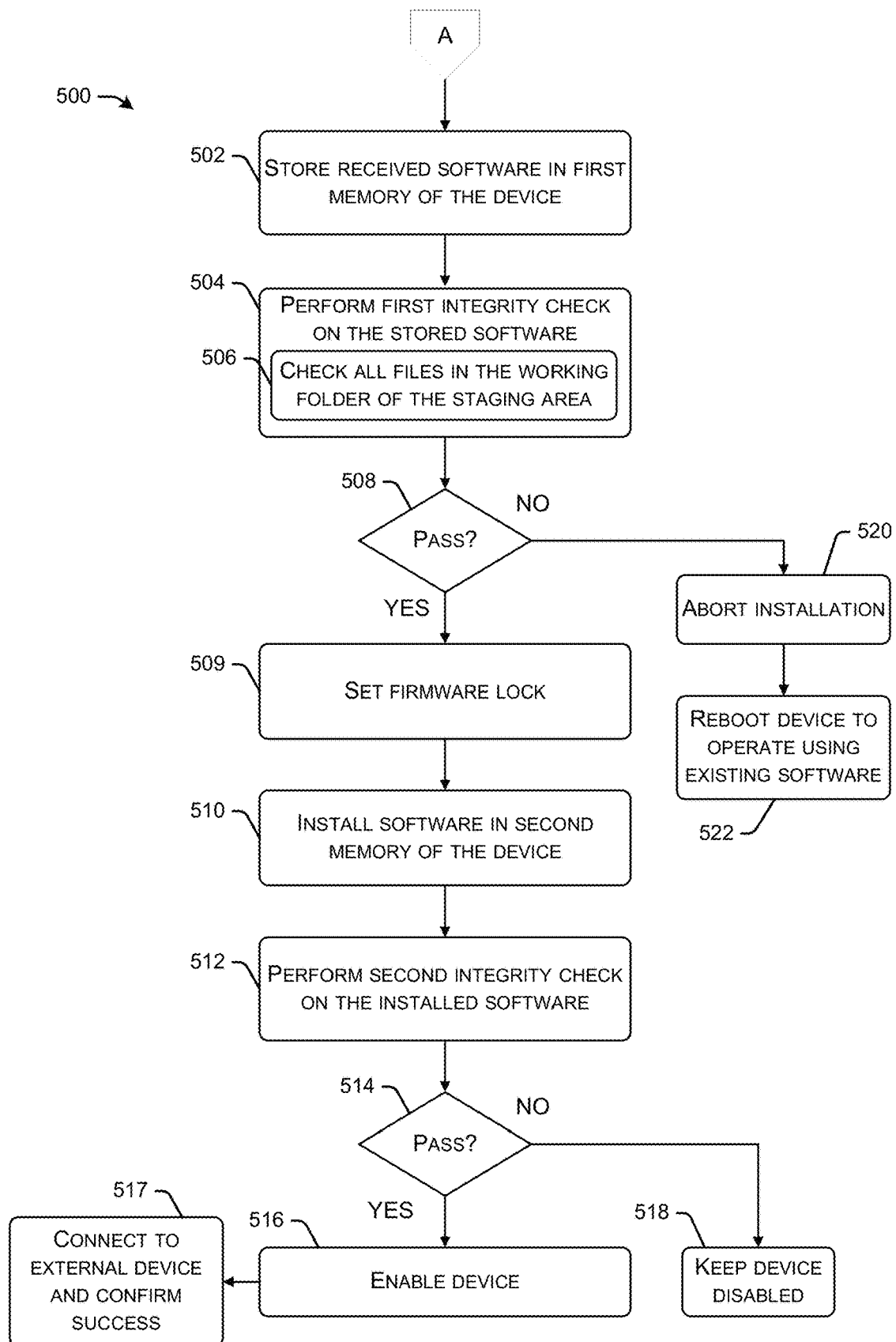
FIG. 5 illustrates an example process for updating software on a device.

FIG. 5 is an example process 500 for updating software on a device 102. In various implementations, the process 500 is performed by an entity such as the device 102 (e.g., a processor(s) of the device 102). Furthermore, as shown by the off-page reference "A" in FIGS. 4 and 5, the process 500, in some examples, continues from block 416 of the process 400.

At 502, the device 102 (e.g., a processor(s) of the device 102) stores software (SW2) 114 received from an external device 104 in the first memory 106 of the device as stored software 114. The stored software 114 is associated with a software update for the device 102. According to some examples, the software 114 is downloaded to a working folder 302(1) within a staging area 300 of the first memory 106. As noted elsewhere herein, the first memory 106, in an example, is a SD card, such as a μSD card.

At 504, the device 102 (e.g., a processor(s) of the device 102) performs a first integrity check 116(1) on the stored software 114, as described herein. In an illustrative example, the device 102, at 504, executes the following checks for each file of the stored/downloaded software 114 in the staging area 300 of the first memory 106: (i) the computed SHA-256 hash code of the file matches what is listed in the manifest file 304; (ii) the software component's part number and software version number (which is integrated in a version file) matches the version number specified in the manifest file 304; and (iii) the CRC for each image in the file matches the CRC listed in the corresponding version file for that image. At sub-block 506, in some examples, the performing of the first integrity check 116(1) involves performing the first integrity check 116(1) on all files in the working folder 302(1) of the staging area 300, which, in some scenarios, includes a copy(ies) of a file(s) that was previously copied to the working folder 302(1) as opposed to being downloaded from the external device 104.

At 508, the device 102 (e.g., a processor(s) of the device 102) determines whether the stored software 114 passed the first integrity check 116(1). If the stored software 114 passed the first integrity check 116(1), the process 500 follows the YES route from 508 to 509 where an "Install Lock" is set into the firmware to disable the device 102 from performing tasks other than completing an install of the software 114. The firmware lock is to be cleared after verification of a successful install.

At 510, the device 102 (e.g., a processor(s) of the device 102) installs the stored software 114 in the second memory 108 as installed software 114 based at least in part on the stored software 114 having passed the first integrity check 116(1). As described herein, the installation at 510, in some examples, involves running install scripts after rebooting the device 102 into install mode. The second memory 108, in some examples, is non-volatile memory different than the first memory 106, such as an HDD or a SDD of the device 102. In some examples, block 510 corresponds to steps 218 through 224 depicted in FIG. 2 and described above.

At 512, the device 102 (e.g., a processor(s) of the device 102) performs a second integrity check 116(2) on the installed software 114. As described herein, the second integrity check 116(2) is performed after rebooting the device 102 into a test mode and as part of running one or more Auto-Tests on the installed software 114. In some examples, the second integrity check 116(2) is similar to the first integrity check 116(1). In some examples, the second integrity check 116(2) is performed during the installation phase as part of a software application that is separate from an install software application. After installation, the this second integrity check can be performed periodically (e.g., daily) to ensure the device 102 did not acquire malware (e.g., a virus or malicious code).

At 514, the device 102 (e.g., a processor(s) of the device 102) determines whether the installed software 114 passed the second integrity check 116(2). In some examples, block 514 corresponds to steps 224 through 234 depicted in FIG. 2 and described above If the installed software 114 passed the second integrity check 116(2), the process 500 follows the YES route from 514 to 516. In some examples, after passing the second integrity check 116(2), the device 102 is rebooted into a setup mode, and the device 102 sends, while in the setup mode, information to the external device 104 indicating that the software update was successful.

At 516, the device 102 is enabled for use based at least in part on the installed software 114 having passed the second integrity check 116(2). In some examples, enabling the device 102 at 516 represents, or includes, clearing the firmware lock that was set at block 509. Clearing the firmware lock enables using the device 102 to boot any of the installed applications. In examples where the device 102 is a medical device, such as a defibrillator, the device 102 can boot an application for use in association with a patient, such as to administer defibrillation therapy to the patient. At 517, the device 102 connects (e.g., re-connects) to an external device 104 (e.g., a server computer 104(1)) and confirms success with respect to the software install (e.g., the device 102 sends information to the external device 104 (e.g., the server computer 104(1)) indicating that the software update was successful.

If, at 514, the installed software 114 did not pass the second integrity check 116(2), the process 500 follows the NO route from 514 to 518, where the device 102 remains disabled (based on the firmware lock that was set at block 509). In this way, the device 102 is inoperable because at least in part on the installed software 114 having not passed the second integrity check 116(2). In a medical setting, this prevents a medical device with compromised software from operating in the field and potentially jeopardizing the safety of a patient. A user may re-try a software install to see if it works on a second attempt. Such a re-try may include power-cycling the device 102, in which case the install is repeated. If the device 102 remains disabled after the second attempt (or any number of additional attempts), then an Initial Software Load may be performed to restore the device 102. The external device 104 may discover that the software update was unsuccessful based on a timeout occurring without the device 102 connecting to the external device 104 and confirming success.

Referring again to block 508, if the device 102 (e.g., a processor(s) of the device 102) determines that the stored software 114 did not pass the first integrity check 116(1), the process 500 follows the NO route from 508 to 520 where the device 102 aborts the installation of the stored software 114 based at least in part on the stored software 114 having not passed the first integrity check 116(1), and the device 102 refrains from installing the stored software 114 in the second memory 108 of the device 102. Notably, the renaming of the folders 302 (described above with reference to FIG. 3) has not yet occurred at a time when the device 102 aborts the installation at block 520. Rather, the renaming of the folders 302 occurs after the firmware lock is set at block 509 in an instance where the process 500 follows the YES route from block 508 to block 509. In some examples, upon aborting the installation at block 520, the device 102 outputs (e.g., displays, emits from a speaker(s), etc.) a notification that the software update was unsuccessful and/or sends information to the external device 104 indicating that the software update was unsuccessful.

At 522, the device 102 reboots so that the device 102 operates using the existing software (SW1) 314(A) that is currently installed in the second memory 108. Accordingly, by holding the stored software 114 in the staging area 300 while the first integrity check 116(1) is performed, the device 102 remains operational by aborting the installation of the software if an issue arises during the first integrity check 116(1).

Accordingly, in one example implementation of the process 500, after installing new software (e.g., the software 114) on a device 102, the device 102 makes sure that the installed software is still good software by performing an integrity check (e.g., the integrity check 116(2)) on the installed software, and further usage of the device 102 is prevented if the device 102 determines that the installed software has been corrupted after installation of the software on the device 102.

Figure 6:
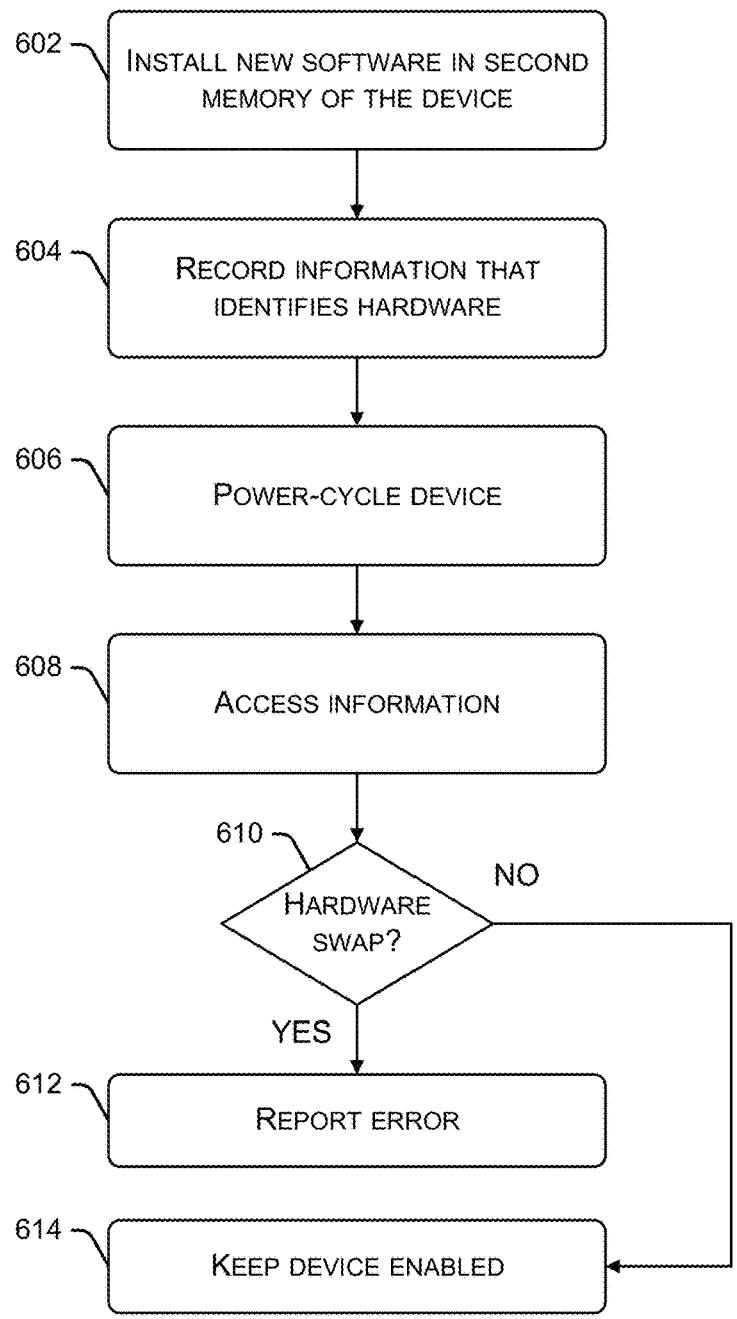
FIG. 6 illustrates an example process for detecting whether hardware has been swapped on a device.

FIG. 6 is an example process 600 for detecting whether hardware has been swapped on a device 102. In various implementations, the process 600 is performed by an entity such as the device 102 (e.g., a processor(s) of the device 102).

At 602, a device 102 (e.g., a processor(s) of the device 102) installs software 114 in second memory 108 of the device 102 as installed software 114. In some examples, the operation(s) performed at 602 include performing the process 500.

At 604, the device 102 (e.g., a processor(s) of the device 102) records information that identifies hardware components that are currently installed in the device 102. In some examples, the recordation of the hardware identifier information represents a hardware audit, such as an inspection performed by the device 102 to identify or otherwise inventory the hardware components installed in, or on, the device 102, and which are configured to operate under the control and/or management of the installed software 114. In an example where the device 102 is a medical device, such as a defibrillator, the information identifies components such as a $SPO_2$ component and a $CO_2$ component, among other components.

At 606, the device 102 is power-cycled. In some examples, a user powers off the device 102 and subsequently powers on the device 102. In some examples, the device 102 boots up after the power cycle at block 606, and the subsequent blocks 608-614 are performed on every boot. That is, on every boot-up of the device 102, a check can be performed to detect the hardware components and/or the software versions that are installed, and a discrepancy can flag an error on the device 102. Periodically (e.g., daily), a more extensive software and hardware verification may be performed to re-check the digital signatures by comparing what is in first memory 106 to what is in second memory 108.

At 608, the device 102 (e.g., a processor(s) of the device 102) accesses the information that was recorded at 604. In an example, the information is accessed from non-volatile memory of the device 102, such as from the second memory 108 of the device 102, as described herein.

At 610, the device 102 (e.g., a processor(s) of the device 102) detects, based on the information, whether a hardware component of the device 102 has been replaced with a different hardware component. In some examples, the device 102 compares serial numbers or the like that are included in the information with current serial numbers read from currently-installed hardware components upon boot-up. If replacement of a hardware component is detected, the process 600 follows the YES route from 610 to 612, where the device 102 reports (e.g., outputs) an error (e.g., a critical error) to recommend that a user contact service. In a medical device example, a user can try to use the device 102 in association with a patient, the device 102 may output a periodic alert (e.g., by beeping regularly) to indicate a problem. This allows the device 102 to be used (e.g., to attempt saving a life of a patient) if it so happens that a transient error occurred, as opposed to an actual failure of the hardware. In some examples, however, the device 102 may be disabled upon detecting a hardware swap at block 610.

If, at 610, the device 102 does not detect that any hardware component has been replaced, the process 600 follows the NO route from 610 to 614, where the device 102 remains enabled for use. In a medical device example, the device 102 remains enabled for use in association with a patient, such as to administer defibrillation therapy thereto.

In some examples, at 610, the device 102 (e.g., a processor(s) of the device 102) performs an integrity check on the hardware component(s), such as by checking a voltage, an impedance, a current, and/or another electrical parameter associated with an individual hardware component to ensure that the hardware component(s) is/are functioning properly. For example, a resistor may have burned out, or other components may have been damaged or worn down over time through usage of the device 102. If the hardware integrity check performed at block 610 results in the identification of a malfunctioning hardware component, the process 600 may follow the YES route from block 610 to block 612 where the device reports an error, regardless of whether a hardware swap is detected at 610 or not. In other words, the device 102 reports an error if either an unauthorized or a deteriorating hardware component is identified. In this scenario, the initial software load (or initial software install) described above with reference to FIG. 1 may be performed to recover from a detected hardware swap. Otherwise, if no unauthorized hardware components are identified and if no deteriorating or malfunctioning hardware components are identified, the device 102 remains enabled at 614 by following the NO route from block 610.

Accordingly, in one example implementation of the process 600, when new software (e.g., the software 114) is installed on a device 102, the device 102 performs a hardware audit and/or a hardware integrity check to ensure that unauthorized hardware components haven't been installed by someone other than the device manufacturer and/or to ensure that the hardware components are functioning properly, and if unauthorized or malfunctioning hardware is identified, a user can be made aware of the hardware issue to contact service.

Figure 7:
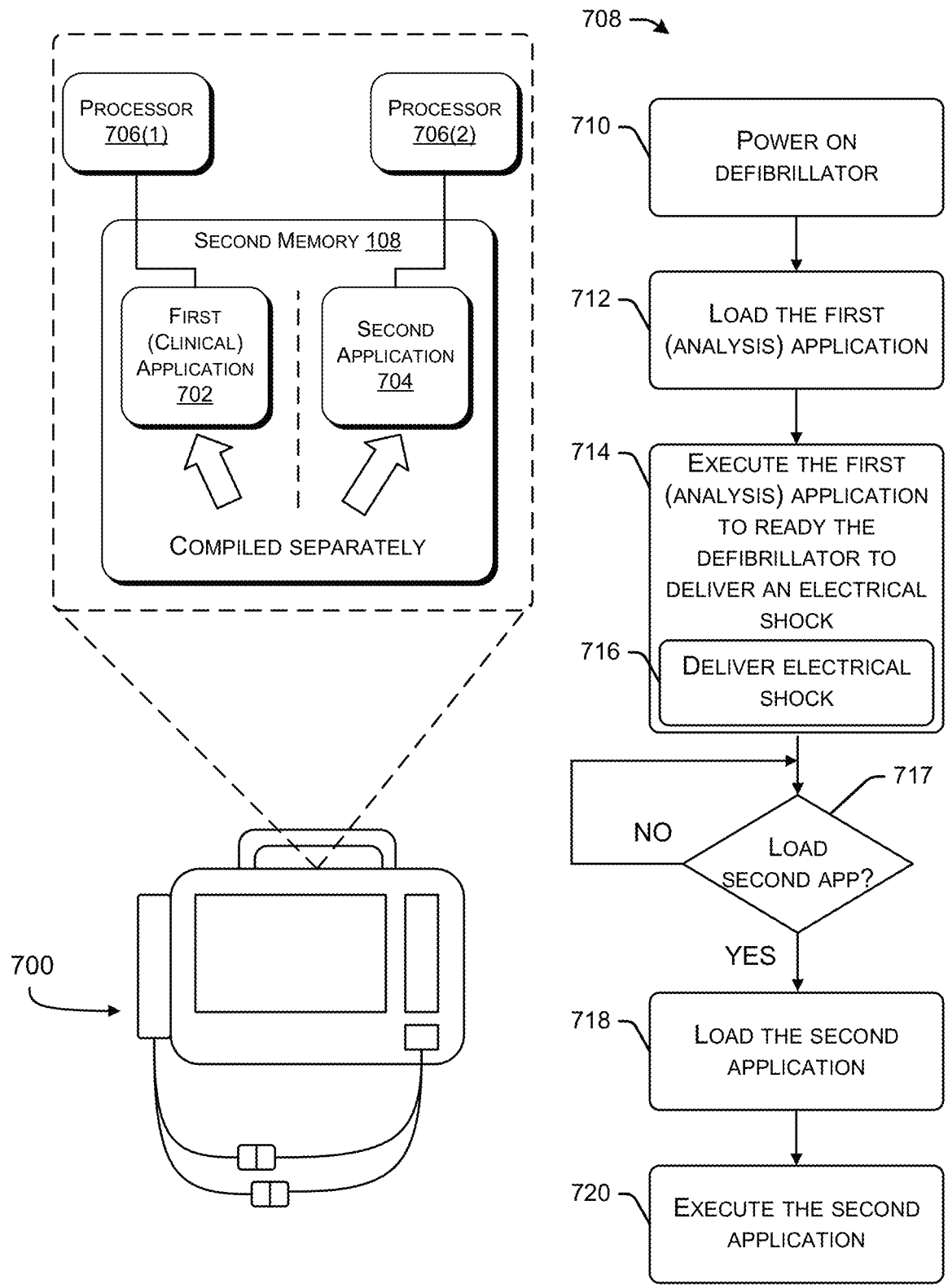
FIG. 7 illustrates an example computer architecture for an external defibrillator and an example process that isolates the execution of software applications installed thereon.

FIG. 7 illustrates an example computer architecture for an external defibrillator 700 and an example process 708. The computer architecture of the external defibrillator 700 isolates the execution of a first software application 702 that is configured to control delivery of an electrical shock via a set of electrodes from the execution of a second software application 704 that is not involved in controlling delivery of the electrical shock to defibrillate a patient, such as to transmit archived data from the device to a hospital. The external defibrillator 700 is an example of the device 102 described elsewhere herein and introduced in FIG. 1. The first software application 702 is sometimes referred to herein as a "clinical application" that is used while the defibrillator 700 is in a mode called a "patient mode." The second software application 704 can be any suitable application, such as, without limitation, an "install application" (e.g., for installing new software), a "setup application" (e.g., for configuring the device 102 while in a "setup mode"), an "archive application" (e.g., for reviewing and transmitting patient data manually), a "transmit application" (e.g., for compressing and managing storage of patient data, and automatically transmitting the data to an external device(s) 104), a "runtest application" (for executing test software), or a "show application" (e.g., for demonstrating device functionality to customers who are considering purchasing the defibrillator 700). These are just example types of second software applications 704, and it is to be appreciated that the second software application 704 can be any other type of application that is not involved in controlling delivery of the electrical shock to defibrillate a patient. The software across packages operates based on the Software Mode (SM) of the system, which can be the same as the device mode, a combination of multiple device modes, or a decomposition of multiple device modes into the software mode. In some examples, one second application 704 may perform a software installation and another second application 704 may perform an integrity check(s) on the installed software, as described herein. For example, the install application (an example of a second application 704) may install new software while the device 102 is in an install mode, and the runtest application may perform the second integrity check after the new software is installed and while the device 102 is in a runtest mode. That provides independence of functionality between installation and integrity checking.

Meanwhile, the clinical application 702 is executed when the defibrillator 700 enters a main mode of operation, such as a "patient mode", in which the clinical application 702 controls the delivery of an electrical shock via a set of electrodes of the defibrillator 700 to defibrillate a patient. In some examples, the main mode of operation (e.g., the patient mode) and any secondary mode of operation (e.g., the setup mode) are mutually exclusive from each other, meaning that the defibrillator 700 does not operate in the patient mode simultaneously with any other secondary mode of operation, such as the setup mode. FIG. 7 illustrates how the execution of the first (clinical) software application 702 on the defibrillator 700 is isolated from the execution of the second software application 704 on the defibrillator 700. According to some examples, the isolation of the execution of each software application 702, 704 is accomplished by compiling the clinical application 702 separately from the setup application 704. In some examples, the source code for each software application 702, 704 is created in a high level programming language independently of the other, and then the independently-created source code is compiled separately so as to eliminate any interdependence of the execution of the clinical application 702 on the execution of the setup application 704, and vice versa. In some examples, the separately-compiled applications 702, 704 are each compiled into machine code that is executable by a processor(s) of the defibrillator 700. This means that the defibrillator 700 (e.g., one or more processors of the defibrillator 700) is configured to execute the first (clinical) software application 702 without executing the second software application 704 (e.g., the setup application), and is configured to execute the second software application 704 without executing the first (clinical) software application 702, which is enabled due to the second software application 704 (e.g., the setup application) being compiled separately from the first (clinical) software application 702. Accordingly, the boundaries, in the software code, between patient mode (associated with the first (clinical) software application 702) and a secondary mode, such as the setup mode (associated with the second software application 704) are distinct, and there is no interdependence of one software application on the other except for the setup application 704 managing software updates for the clinical application 702.

According to some examples, these separately-compiled software applications 702, 704 are executable by the same (single) processor 706, although FIG. 7 illustrates an example where the software applications 702, 704 are executable by different processors of the defibrillator 700. For example, the defibrillator 700 includes multiple processors 706 including a first processor 706(1) and a second processor 706(2). The first processor 706(1) is configured to execute the clinical application 702 and the second processor 706(2) is configured to execute the setup application 704. A dedicated processor 706 for executing a separately-compiled software application (e.g., either the first software application 702 or the second software application 704) may help isolate the execution of the software applications 702, 704 on the defibrillator 700. Among other things, isolating the execution of the clinical application 702 from the execution of the setup application 704—through separately-compiled code—allows the defibrillator 700 to be "brought online" faster when the defibrillator 700 is powered on (from a powered off state) due at least in part to the ability of a processor 706 to load the clinical application 702 without having to load the setup application 704 before the defibrillator 700 is ready to deliver a shock via the set of electrodes of the defibrillator 700. Initially, when the defibrillator 700 is first powered on, the initial functioning software application is the first (clinical) software application 702. This allows the defibrillator 700 to decrease the time it takes to treat a patient after the defibrillator 700 is turned on, which could be a life-saving feature in many cases. In some examples, on power-up, the defibrillator 700 loads the code of the clinical application 702 to be able to deliver a shock within a threshold amount of time (e.g., within 10 seconds) of power-up. This, in part, is due to the isolation of the execution of the clinical application 702 from the execution of other applications, such as the setup application 704, on the defibrillator 700.

FIG. 7 illustrates an example process 708 of operating the defibrillator 700 with the first and second applications 702, 704 installed thereon. At 710, the defibrillator 700 is powered on. For example, the user presses a power button or actuates a power switch to power on the defibrillator 700.

At 712, the external defibrillator 700 (e.g., a processor 706, such as the first processor 706(1)) loads the first software application 702. In some examples, the loading at 712 includes loading the first software application 702 into working memory (e.g., RAM) of the defibrillator 700.

At 714, the external defibrillator 700 (e.g., the first processor 706(1)) executes the first software application 702 to ready the external defibrillator 700 to deliver the electrical shock. In some examples, readying the external defibrillator 700 to deliver the electrical shock includes the first processor 706(1) activating a charging switch in a charging circuit of the defibrillator 700 connect a power source of the defibrillator 700 with a capacitor of the defibrillator, and charging the capacitor with the power source. These features of the defibrillator 700 are described in more detail below with reference to FIG. 8. According to some examples, the external defibrillator 700 is readied to deliver the electrical shock within a threshold amount of time from/since powering on the external defibrillator 700 at 710.

At 716, the external defibrillator 700 (e.g., the first processor 706(1) executing the first software application 702) delivers an electrical shock via the set of electrodes of the defibrillator 700, if an electrical shock is needed. By isolating the execution of the first and second software applications 702, 704, the external defibrillator 700 is configured to ready itself for delivery of the electrical shock quickly. Furthermore, the external defibrillator 700 operates in a main mode of operation (e.g., a patient mode) at block 714 while the first (clinical) software application 702 is executed by a processor 706 of the defibrillator 700.

At 717, after readying the external defibrillator 700 to deliver the electrical shock, a determination is made as to whether to load a second software application 704. In an example, the determination at 717 is based on receiving user input at the defibrillator 700 to operate the defibrillator 700 in a different mode of operation that does not involve defibrillation therapy, such as if a user navigates to a menu on a display of the defibrillator 700 to enter the setup mode of the defibrillator 700. In another example, the determination at 717 is based on the readiness of the defibrillator 700 to deliver an electrical shock or passage of time. If the determination at 717 is to refrain from loading the second software application 704, the process 708 follows the NO route from 717 to iterate the determination at 717. This may occur if the defibrillator 700 is still being used to administer defibrillation therapy to a patient, for example. If the determination at 717 is to load the second software application 704, the process 708 follows the YES route from 717 to 718.

At 718, the external defibrillator 700 (e.g., the second processor 706(2)) loads the second software application 704. The second software application is the setup application, in some examples, allowing a user to change settings of the defibrillator 700 and/or manage software updates for the first software application 702 (e.g., the clinical application 702).

At 720, the external defibrillator 700 (e.g., the second processor 706(2)) executes the second software application 704. Again, the second software application 704 is executable to change settings of the defibrillator 700 and/or manage software updates for the external defibrillator 700 (e.g., installing a new version of the first software application 702 on the external defibrillator 700).

Accordingly, in one example implementation of the process 708, when a defibrillator 700 is initialized, the defibrillator 700 exclusively initializes the software applications/modules necessary for administering therapy to minimize the time-to-shock, among other things, and the defibrillator 700 leaves other software applications/modules uninitialized, but the user can initialize the other software applications independently in order to operate the defibrillator 700 in other non-therapy modes, as needed.

Figure 8:
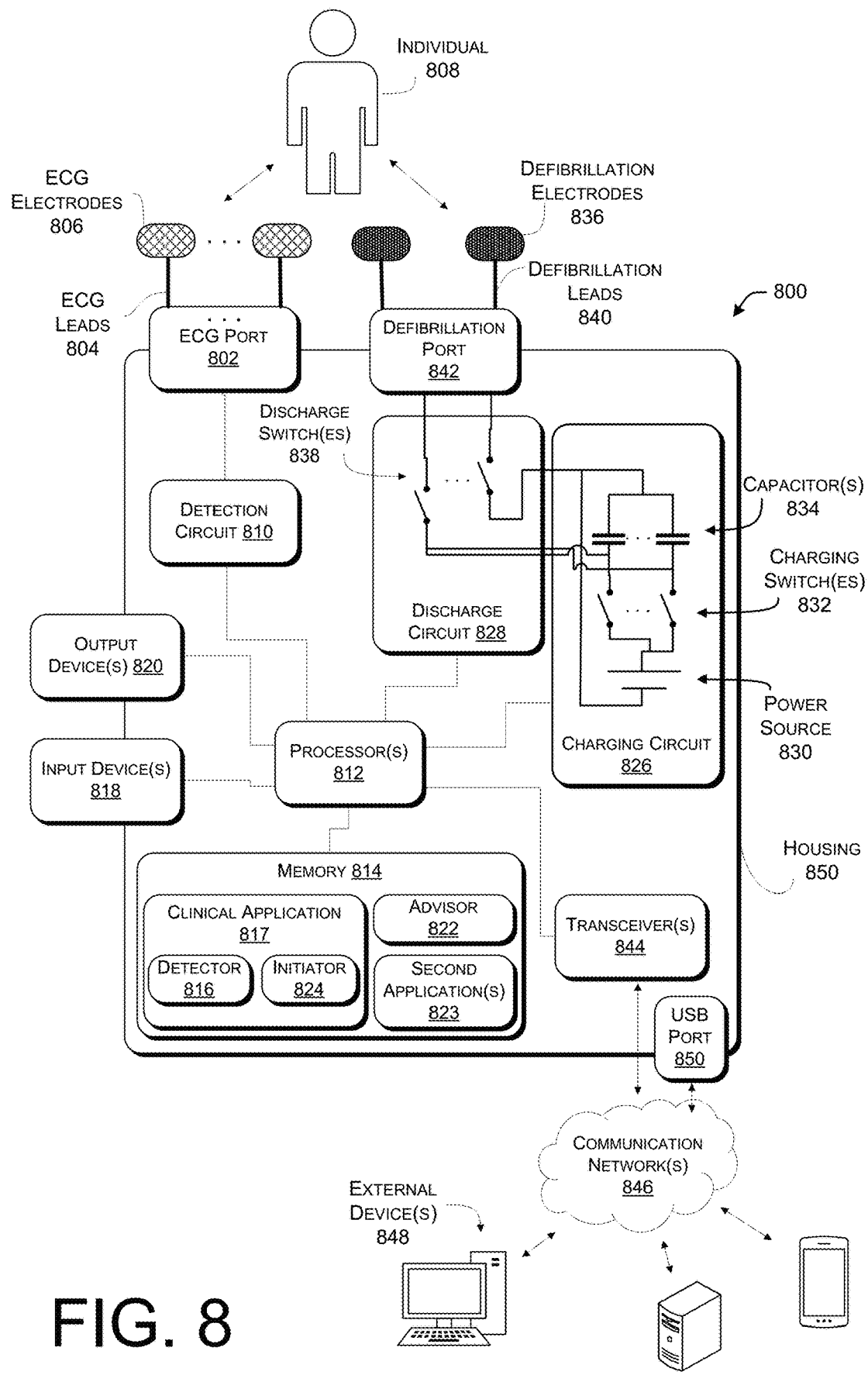
FIG. 8 illustrates an example external defibrillator configured to perform various functions described herein.

FIG. 8 illustrates an example of an external defibrillator 800 configured to perform various functions described herein. For example, the external defibrillator 800 is an example of the device 102 described elsewhere herein and introduced in FIG. 1. In some examples, the defibrillator 800 represents the defibrillator 700 of FIG. 7.

The external defibrillator 800 includes an electrocardiogram (ECG) port 802 connected to multiple ECG leads 804. In some cases, the ECG leads 804 are removeable from the ECG port 802. For instance, the ECG leads 804 are plugged into the ECG port 802. The ECG leads 804 are connected to ECG electrodes 806, respectively. In various implementations, the ECG electrodes 806 are disposed on different locations on an individual 808 (e.g., a patient). A detection circuit 810 is configured to detect relative voltages between the ECG electrodes 806. These voltages are indicative of the electrical activity of the heart of the individual 808.

In various implementations, the ECG electrodes 806 are in contact with the different locations on the skin of the individual 808. In some examples, a first one of the ECG electrodes 806 is placed on the skin between the heart and right arm of the individual 808, a second one of the ECG electrodes 806 is placed on the skin between the heart and left arm of the individual 808, and a third one of the ECG electrodes 806 is placed on the skin between the heart and a leg (either the left leg or the right leg) of the individual 808. In these examples, the detection circuit 810 is configured to measure the relative voltages between the first, second, and third ECG electrodes 806. Respective pairings of the ECG electrodes 806 are referred to as "leads," and the voltages between the pairs of ECG electrodes 806 are known as "lead voltages." In some examples, more than three ECG electrodes 806 are included, such that 5-lead or 12-lead ECG signals are detected by the detection circuit 810.

The detection circuit 810 includes at least one analog circuit, at least one digital circuit, or a combination thereof. The detection circuit 810 receives the analog electrical signals from the ECG electrodes 806, via the ECG port 802 and the ECG leads 804. In some cases, the detection circuit 810 includes one or more analog filters configured to filter noise and/or artifact from the electrical signals. The detection circuit 810 includes an analog-to-digital (ADC) in various examples. The detection circuit 810 generates a digital signal indicative of the analog electrical signals from the ECG electrodes 806. This digital signal can be referred to as an "ECG signal" or an "ECG."

In some cases, the detection circuit 810 further detects an electrical impedance between at least one pair of the ECG electrodes 806. For example, the detection circuit 810 includes, or otherwise controls, a power source that applies a known voltage across a pair of the ECG electrodes 806 and detects a resultant current between the pair of the ECG electrodes 806. The impedance is generated based on the applied voltage and the resultant current. In various cases, the impedance corresponds to respiration of the individual 808, chest compressions performed on the individual 808, and other physiological states of the individual 808. In various examples, the detection circuit 810 includes one or more analog filters configured to filter noise and/or artifact from the resultant current. The detection circuit 810 generates a digital signal indicative of the impedance using an ADC. This digital signal can be referred to as an "impedance signal" or an "impedance."

The detection circuit 810 provides the ECG signal and/or the impedance signal to one or more processors 812 in the external defibrillator 800. In some implementations, the processor(s) 812 includes a central processing unit (CPU), a graphics processing unit (GPU), both CPU and GPU, or other processing unit or component known in the art. In some examples, the processor(s) 812 represents multiple processors, such as the processors 706 described with reference to FIG. 7. That is, the processor(s) 812, in some examples, include the first processor 706(1) and the second processor 706(2), and potentially additional processors. In some examples, multiple processors 812 can include a system processor (e.g., a main CPU) and multiple dedicated or specialty processors for particular purposes (e.g., power management, therapy, paddle sensing, user interface, vital signs, etc.).

The processor(s) 812 is operably connected to memory 814. In various implementations, the memory 814 includes volatile (such as random access memory (RAM)), non-volatile (such as read only memory (ROM), flash memory, etc.) or some combination of the two. In some examples, the memory 814 represents, or includes, the first memory 106 and the second memory 108 described herein. The memory 814, in some examples, further includes "working" memory, such as RAM, where applications (e.g., the clinical application 702, etc.) are loaded for execution on the defibrillator 800. In general, the memory 814 stores instructions that, when executed by the processor(s) 812, causes the processor(s) 812 to perform various operations. In various examples, the memory 814 stores methods, threads, processes, applications, objects, modules, any other sort of executable instruction, or a combination thereof. In some cases, the memory 814 stores files, databases, or a combination thereof. In some examples, the memory 814 includes, but is not limited to, RAM, ROM, EEPROM, flash memory, or any other memory technology. In some examples, the memory 814 includes one or more of CD-ROMs, digital versatile discs (DVDs), content-addressable memory (CAM), or other optical storage, magnetic cassettes, magnetic tape, magnetic disk storage or other magnetic storage devices, or any other medium which can be used to store the desired information and which can be accessed by the processor(s) 812 and/or the external defibrillator 800. In some cases, the memory 814 at least temporarily stores the ECG signal and/or the impedance signal.

In various examples, the memory 814 includes a detector 816, which causes the processor(s) 812 to determine, based on the ECG signal and/or the impedance signal, whether the individual 808 is exhibiting a particular heart rhythm. For instance, the processor(s) 812 determines whether the individual 808 is experiencing a shockable rhythm that is treatable by defibrillation. Examples of shockable rhythms include ventricular fibrillation (VF) and pulseless ventricular tachycardia (V-Tach). In some examples, the processor(s) 812 determines whether any of a variety of different rhythms (e.g., asystole, sinus rhythm, atrial fibrillation (AF), etc.) are present in the ECG signal. In some examples, the detector 816 represents, or is at least part of, a clinical application 817, which may be the same as, or similar to, the first software application 702 depicted in FIG. 7 and described in detail above.

The processor(s) 812 is operably connected to one or more input devices 818 and one or more output devices 820. Collectively, the input device(s) 818 and the output device(s) 820 function as an interface between a user and the defibrillator 800. The input device(s) 818 is configured to receive an input from a user and includes at least one of a keypad, a cursor control, a touch-sensitive display, a voice input device (e.g., a speaker), a haptic feedback device, or any combination thereof. The output device(s) 820 includes at least one of a display, a speaker, a haptic output device, a printer, or any combination thereof. In various examples, the processor(s) 812 causes a display among the input device(s) 818 to visually output a waveform of the ECG signal and/or the impedance signal. In some implementations, the input device(s) 818 includes one or more touch sensors, the output device(s) 820 includes a display screen, and the touch sensor(s) are integrated with the display screen. Thus, in some cases, the external defibrillator 800 includes a touchscreen configured to receive user input signal(s) and visually output physiological parameters, such as the ECG signal and/or the impedance signal.

In some examples, the memory 814 includes an advisor 822, which, when executed by the processor(s) 812, causes the processor(s) 812 to generate advice and/or control the output device(s) 820 to output the advice to a user (e.g., a rescuer). In some examples, the processor(s) 812 provides, or causes the output device(s) 820 to provide, an instruction to perform CPR on the individual 808. In some cases, the processor(s) 812 evaluates, based on the ECG signal, the impedance signal, or other physiological parameters, CPR being performed on the individual 808 and causes the output device(s) 820 to provide feedback about the CPR in the instruction. According to some examples, the processor(s) 812, upon identifying that a shockable rhythm is present in the ECG signal, causes the output device(s) 820 to output an instruction and/or recommendation to administer a defibrillation shock to the individual 808.

In some examples, the memory 814 includes a second application(s) 823 which may correspond to the second software application 704 depicted in FIG. 7, or multiple second software applications 704, and is described in detail above. For example, the second application 823 may be configured to change settings of the defibrillator 700 and/or manage software updates for the external defibrillator 700 (e.g., by managing the installation of a new version of the clinical application 817 on the external defibrillator 700). In general, the software packages stored in the memory 814 may form the list of files 306 that are in the manifest file 304, which is described in more detail elsewhere herein.

The memory 814 also includes an initiator 824 which, when executed by the processor(s) 812, causes the processor(s) 812 to control other elements of the external defibrillator 800 in order to administer a defibrillation shock to the individual 808. In some examples, the processor(s) 812 executing the initiator 824 selectively causes the administration of the defibrillation shock based on determining that the individual 808 is exhibiting the shockable rhythm and/or based on an input from a user (received, e.g., by the input device(s) 818). In some cases, the processor(s) 812 causes the defibrillation shock to be output at a particular time, which is determined by the processor(s) 812 based on the ECG signal and/or the impedance signal. In some examples, the initiator 824 represents, or is at least part of, the clinical application 817, which may be the same as, or similar to, the first software application 702 depicted in FIG. 7 and described in detail above.

The processor(s) 812 is operably connected to a charging circuit 826 and a discharge circuit 828. In various implementations, the charging circuit 826 includes a power source 830, one or more charging switches 832, and one or more capacitors 834. The power source 830 includes, for instance, a battery. The processor(s) 812 initiates a defibrillation shock by causing the power source 830 to charge at least one capacitor among the capacitor(s) 834. For example, the processor(s) 812 activates at least one of the charging switch(es) 832 in the charging circuit 826 to complete a first circuit connecting the power source 830 and the capacitor 834 to be charged. Then, the processor(s) 812 causes the discharge circuit 828 to discharge energy stored in the charged capacitor 834 across a pair of defibrillation electrodes 836, which are in contact with the individual 808. For example, the processor(s) 812 deactivates the charging switch(es) 832 completing the first circuit between the capacitor(s) 834 and the power source 830, and activates one or more discharge switches 838 completing a second circuit connecting the charged capacitor 834 and at least a portion of the individual 808 disposed between defibrillation electrodes 836.

The energy is discharged from the defibrillation electrodes 836 in the form of a defibrillation shock. For example, the defibrillation electrodes 836 are connected to the skin of the individual 808 and located at positions on different sides of the heart of the individual 808, such that the defibrillation shock is applied across the heart of the individual 808. The defibrillation shock, in various examples, depolarizes a significant number of heart cells in a short amount of time. The defibrillation shock, for example, interrupts the propagation of the shockable rhythm (e.g., VF or V-Tach) through the heart. In some examples, the defibrillation shock is 200 joules (J) or greater with a duration of about 0.015 seconds. In some cases, the defibrillation shock has a multiphasic (e.g., biphasic) waveform. The discharge switch(es) 838 are controlled by the processor(s) 812, for example. In various implementations, the defibrillation electrodes 836 are connected to defibrillation leads 840. The defibrillation leads 840 are connected to a defibrillation port 842, in implementations. According to various examples, the defibrillation leads 840 are removable from the defibrillation port 842. For example, the defibrillation leads 840 are plugged into the defibrillation port 842.

In various implementations, the processor(s) 812 is operably connected to one or more transceivers 844 and/or a wired universal serial bus (USB) connection/port 850 to transmit and/or receive data over one or more communication networks 846. For example, the transceiver(s) 844 includes a network interface card (NIC), a network adapter, a local area network (LAN) adapter, or a physical, virtual, or logical address to connect to the various external devices and/or systems. In various examples, the transceiver(s) 844 includes any sort of wireless transceivers capable of engaging in wireless communication (e.g., radio frequency (RF) communication). For example, the communication network(s) 846 includes one or more wireless networks that include a 3rd Generation Partnership Project (3GPP) network, such as a Long Term Evolution (LTE) radio access network (RAN) (e.g., over one or more LE bands), a New Radio (NR) RAN (e.g., over one or more NR bands), or a combination thereof. In some cases, the transceiver(s) 844 includes other wireless modems, such as a modem for engaging in WI-FI®, WIGIG®, WIMAX®, BLUETOOTH®, or infrared communication over the communication network(s) 846. The wired USB port 850 may be used for the initial software load as part of a 'locked' (e.g., secure) software installation.

The defibrillator 800 is configured to transmit and/or receive data (e.g., ECG data, impedance data, data indicative of one or more detected heart rhythms of the individual 808, data indicative of one or more defibrillation shocks administered to the individual 808, etc.) with one or more external devices 848 via the communication network(s) 846. In some examples, the external devices 848 represent, or include, the external devices 104 introduced in FIG. 1. The external devices 848 include, for instance, mobile devices (e.g., mobile phones, smart watches, etc.), Internet of Things (IoT) devices, medical devices, computers (e.g., laptop devices, servers, etc.), or any other type of computing device configured to communicate over the communication network(s) 846. In some examples, the external device(s) 848 is located remotely from the defibrillator 800, such as at a remote clinical environment (e.g., a hospital). According to various implementations, the processor(s) 812 causes the transceiver(s) 844 to transmit data to the external device(s) 848. In some cases, the transceiver(s) 844 receives data from the external device(s) 848 and the transceiver(s) 844 provide the received data to the processor(s) 812 for further analysis.

In various implementations, the external defibrillator 800 also includes a housing 850 that at least partially encloses other elements of the external defibrillator 800. For example, the housing 850 encloses the detection circuit 810, the processor(s) 812, the memory 814, the charging circuit 826, the transceiver(s) 844, or any combination thereof. In some cases, the input device(s) 818 and output device(s) 820 extend from an interior space at least partially surrounded by the housing 850 through a wall of the housing 850. In various examples, the housing 850 acts as a barrier to moisture, electrical interference, and/or dust, thereby protecting various components in the external defibrillator 800 from damage.

In some implementations, the external defibrillator 800 is an automated external defibrillator (AED) operated by an untrained user (e.g., a bystander, layperson, etc.) and can be operated in an automatic mode. In automatic mode, the processor(s) 812 automatically identifies a rhythm in the ECG signal, makes a decision whether to administer a defibrillation shock, charges the capacitor(s) 834, discharges the capacitor(s) 834, or any combination thereof. In some cases, the processor(s) 812 controls the output device(s) 820 to output (e.g., display) a simplified user interface to the untrained user. For example, the processor(s) 812 refrains from causing the output device(s) 820 to display a waveform of the ECG signal and/or the impedance signal to the untrained user, in order to simplify operation of the external defibrillator 800.

In some examples, the external defibrillator 800 is a monitor-defibrillator utilized by a trained user (e.g., a clinician, an emergency responder, etc.) and can be operated in a manual mode or the automatic mode. When the external defibrillator 800 operates in manual mode, the processor(s) 812 cause the output device(s) 820 to display a variety of information that is relevant to the trained user, such as waveforms indicating the ECG data and/or impedance data, notifications about detected heart rhythms, and the like.

Example Clauses

1. An external defibrillator including: a processor; first memory; and second memory storing computer-executable instructions that, when executed by the processor, cause performance of operations including: downloading software from an external device to the first memory as downloaded software, the downloaded software associated with a software update for the external defibrillator; performing a first integrity check on the downloaded software; determining that the downloaded software passed the first integrity check; based on the downloaded software having passed the first integrity check, installing the downloaded software in the second memory as installed software; and performing a second integrity check on the installed software.
2. The external defibrillator of clause 1, wherein the operations further include: determining that the installed software passed the second integrity check; and enabling the external defibrillator for use in association with a patient based on the installed software having passed the second integrity check.
3. The external defibrillator of clause 1 or 2, wherein the operations further include: determining that the installed software did not pass the second integrity check; and disabling the external defibrillator so that the external defibrillator is inoperable in association with a patient based on the installed software having not passed the second integrity check.
4. The external defibrillator of any one of clauses 1 to 3, wherein: the first memory includes a Secure Digital (SD) card; and the second memory includes non-volatile memory different than the SD card.
5. The external defibrillator of any one of clauses 1 to 4, wherein the first memory organizes data within a staging area that includes, prior to the installing of the downloaded software in the second memory: a current folder containing a copy of existing software that is currently installed in the second memory; and a working folder containing the downloaded software.
6. The external defibrillator of clause 5, wherein the operations further include, prior to the downloading of the software: receiving a digitally-signed manifest file from the external device that specifies a list of files included in the software update; determining that a first file in the list of files matches a second file of the copy of the existing software in the current folder; storing a copy of the second file in the working folder; performing a preliminary integrity check on the copy of the second file; and determining that the copy of the second file passed the preliminary integrity check; wherein the software downloaded from the external device excludes the first file, and wherein the performing of the first integrity check further includes performing the first integrity check on the copy of the second file.
7. The external defibrillator of any one of clauses 1 to 6, wherein the operations further include, after the installing of the downloaded software in the second memory: recording information that identifies hardware components that are currently installed in the external defibrillator; powering off the external defibrillator; powering on the external defibrillator into a patient mode;

detecting, based on the information, that a hardware component of the hardware components has been replaced with a different hardware component; and disabling the external defibrillator so that the external defibrillator is temporarily unusable in association with a patient.

8. A device including: a processor; first memory; and second memory storing computer-executable instructions that, when executed by the processor, cause performance of operations including: storing software received from an external device in the first memory as stored software, the stored software associated with a software update for the device; performing a first integrity check on the stored software; determining that the stored software passed the first integrity check; based on the stored software having passed the first integrity check, installing the stored software in the second memory as installed software; and performing a second integrity check on the installed software.

9. The device of clause 8, wherein the operations further include: determining that the installed software passed the second integrity check; and enabling the device for use based on the installed software having passed the second integrity check.

10. The device of clause 9, wherein the device is a medical device, and wherein the enabling the device includes enabling the medical device for use in association with a patient.

11. The device of any one of clauses 8 to 10, wherein the operations further include: determining that the installed software did not pass the second integrity check; and disabling the device so that the device is inoperable based on the installed software having not passed the second integrity check.

12. The device of any one of clauses 8 to 11, wherein the first memory organizes data within a staging area that includes, prior to the installing of the stored software in the second memory: a first folder containing a copy of existing software that is currently installed in the second memory; and a second folder containing the stored software.

13. The device of clause 12, wherein the operations further include, prior to the storing of the software: receiving a digitally-signed manifest file from the external device that specifies a list of files included in the software update; determining that a first file in the list of files matches a second file of the copy of the existing software in the first folder; storing a copy of the second file in the second folder; performing a preliminary integrity check on the copy of the second file; determining that the copy of the second file passed the preliminary integrity check; and receiving, from the external device, the software excluding the first file, wherein the performing of the first integrity check further includes performing the first integrity check on the copy of the second file.

14. The device of any one of clauses 8 to 13, wherein the operations further include, after the installing of the stored software in the second memory: recording information that identifies hardware components that are currently installed in the device; powering off the device; powering on the device; detecting, based on the information, that a hardware component of the hardware components has been replaced with a different hardware component; and disabling the device so that the device is temporarily unusable based on the detecting that the hardware component has been replaced.

15. A method including: downloading software to first memory of a device as downloaded software, the downloaded software associated with a software update for the device; performing, by the device, a first integrity check on the downloaded software; determining, by the device, that the downloaded software passed the first integrity check; based on the downloaded software having passed the first integrity check, installing the downloaded software in second memory of the device as installed software; and performing, by the device, a second integrity check on the installed software prior to enabling the device to execute the installed software to operate the device.

16. The method of clause 15, further including, after the installing of the downloaded software, rebooting the device into a test mode, wherein the second integrity check is performed while the device is in the test mode.

17. The method of clause 15 or 16, further including: determining, by the device, that the installed software passed the second integrity check; and enabling the device for use based on the installed software having passed the second integrity check.

18. The method of any one of clauses 15 to 17, further including, after the determining that the installed software passed the second integrity check: rebooting the device into a setup mode; and sending, while the device is in the setup mode, information to a server computer indicating that the software update was successful.

19. The method of any one of clauses 15 to 17, further including: determining, by the device, that the installed software did not pass the second integrity check; disabling the device so that the device is temporarily unusable to execute the installed software based on the installed software having not passed the second integrity check; and sending information to a server computer indicating that the software update was unsuccessful.

20. The method of any one of clauses 15 to 17, further including, prior to the downloading of the software: receiving, at the device, a digitally-signed manifest file that specifies a list of files included in the software update; determining, by the device, that a first file in the list of files matches a second file of existing software that is currently installed on the device; performing, by the device, a preliminary integrity check on a copy of the second file that is stored in the first memory; and determining, by the device, that the copy of the second file passed the preliminary integrity check, wherein the software downloaded to the first memory excludes the first file, and wherein the performing of the first integrity check further includes performing the first integrity check on the copy of the second file.

21. The method of any one of clauses 15 to 17, wherein the device is a medical device, and wherein the enabling the device includes enabling the medical device to execute the installed software to operate the medical device in association with a patient.

22. A device including: a processor; first memory; and second memory storing computer-executable instructions that, when executed by the processor, cause performance of operations including: storing software received from an external device in the first memory as stored software, the stored software associated with a software update for the device; performing an integrity check on the stored software; determining that the stored software did not pass the integrity check; based on the stored software having not passed the integrity check, refraining from installing the stored software in the second memory; outputting a notification that the software update was unsuccessful; and rebooting the device to operate the device using existing software that is installed in the second memory.

23. The device of clause 22, wherein the device is a medical device, and wherein rebooting the device to operate the device includes rebooting the medical device to operate the medical device in association with a patient.

24. The device of clause 22 or 23, wherein the first memory organizes data within a staging area that includes: a first folder containing a copy of the existing software; and a second folder containing the stored software.

25. The device of clause 24, wherein the operations further include, prior to the storing of the software: receiving a digitally-signed manifest file from the external device that specifies a list of files included in the software update; determining that a first file in the list of files matches a second file of the copy of the existing software in the first folder; storing a copy of the second file in the second folder; performing a preliminary integrity check on the copy of the second file; determining that the copy of the second file passed the preliminary integrity check; and downloading the software to the second folder, the software excluding the first file, wherein the performing of the integrity check further includes performing the integrity check on the copy of the second file.

26. An external defibrillator including: a set of electrodes; a processor; and memory storing: a first software application that, when executed by the processor, controls delivery of an electrical shock via the set of electrodes to defibrillate a patient; and a second software application that, when executed by the processor, is not involved in controlling the delivery of the electrical shock, wherein, prior to installation of the first software application and the second software application on the external defibrillator, the second software application was compiled separately from the first software application in order to isolate execution of the first software application on the external defibrillator from execution of the second software application on the external defibrillator.

27. The external defibrillator of clause 26, wherein, upon powering on the external defibrillator, the processor is configured to load the first software application before the processor starts loading the second software application so that the first software application is ready to control delivery of the electrical shock within a threshold amount of time from the powering on of the external defibrillator.

28. The external defibrillator of clause 26 or 27, wherein the second software application, when executed by the processor, displays a home screen on a display of the external defibrillator to allow a user to navigate a menu of setup options including a manual mode setup option and an automated external defibrillator (AED) mode setup option.

29. The external defibrillator of any one of clauses 26 to 28, wherein the second software application, when executed by the processor, is further configured to manage a software update for the external defibrillator, wherein the software update is for installing a new version of the first software application on the external defibrillator.

30. The external defibrillator of clause 29, wherein the second software application is configured to perform a download phase of the software update prior to installing the new version of the first software application on the external defibrillator.

31. The external defibrillator of clause 29 or 30, wherein the external defibrillator is configured to perform multiple integrity checks on the new version of the first software application prior to installing the new version of the first software application on the external defibrillator.

32. An external defibrillator including: a set of electrodes; and memory storing: a first software application that, when executed on the external defibrillator, controls delivery of an electrical shock via the set of electrodes to defibrillate a patient; and a second software application that, when executed on the external defibrillator, is not involved in controlling the delivery of the electrical shock, wherein the second software application was compiled separately from the first software application prior to installation of the first software application and the second software application on the external defibrillator.

33. The external defibrillator of clause 32, further including a first processor and a second processor, wherein the first software application is executable by the first processor and the second software application is executable by the second processor.

34. The external defibrillator of clause 32, further comprising a processor, wherein, upon powering on the external defibrillator, the processor is configured to load the first software application before the processor starts loading the second software application so that the first software application is ready to control delivery of the electrical shock within a threshold amount of time from the powering on of the external defibrillator.

35. The external defibrillator of any one of clauses 32 to 34, wherein the second software application, when executed on the external defibrillator, is further configured to manage a software update for the external defibrillator, wherein the software update is for installing a new version of the first software application on the external defibrillator.

36. The external defibrillator of clause 35, wherein the second software application is configured to perform a download phase of the software update prior to installing the new version of the first software application on the external defibrillator.

37. The external defibrillator of clause 35 or 36, wherein the external defibrillator is configured to perform multiple integrity checks on the new version of the first software application prior to installing the new version of the first software application on the external defibrillator.

38. A method including: powering on an external defibrillator, the external defibrillator having installed thereon: a first software application configured to control delivery of an electrical shock via a set of electrodes of the external defibrillator to defibrillate a patient; and a second software application compiled separately from the first software application, wherein the second software application is not involved in controlling the delivery of the electrical shock; loading, by the external defibrillator, the first software application; and executing, by the external defibrillator, the first software application to ready the external defibrillator to deliver the electrical shock.

39. The method of clause 38, wherein the executing the first software application readies the external defibrillator to deliver the electrical shock within a threshold amount of time from the powering on of the external defibrillator.

40. The method of clause 38 or 39, further including delivering an electrical shock via the set of electrodes.

41. The method of any one of clauses 38 to 40, wherein the external defibrillator includes a first processor and a second processor, wherein the executing the first software application is performed by the first processor, and the second software application is executable by the second processor.

42. The method of any one of clauses 38 to 41, further including loading, by the external defibrillator, the second software application after readying the external defibrillator to deliver the electrical shock.

43. The method of clause 42, further including executing, by the external defibrillator, the second software application to manage a software update for the external defibrillator, wherein the software update is for installing a new version of the first software application on the external defibrillator.

44. The method of clause 42, wherein the second software application is configured to allow a user of the external defibrillator to change settings of the external defibrillator, and wherein the settings comprise settings for synchronized cardioversion and manual defibrillation.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realizing the disclosed techniques and systems in diverse forms thereof.

As will be understood by one of ordinary skill in the art, each implementation disclosed herein can comprise, consist essentially of or consist of its particular stated element, step, or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the implementation to the specified elements, steps, ingredients or components and to those that do not materially affect the implementation. As used herein, the term "based on" is equivalent to "based at least partly on," unless otherwise specified.

The invention claimed is:

1. A device comprising:
    a processor;
    first memory; and
    second memory storing computer-executable instructions that, when executed by the processor, cause performance of operations comprising:
        downloading software from an external device to the first memory as downloaded software, the downloaded software associated with a software update for the device;
        performing a first integrity check on the downloaded software;
        determining that the downloaded software passed the first integrity check;
        based on the downloaded software having passed the first integrity check, installing the downloaded software in the second memory as installed software;
        performing a second integrity check on the installed software;
        determining that the installed software did not pass the second integrity check; and
        disabling the device so that the device is inoperable in association with a patient based on the installed software having not passed the second integrity check.

2. The device of claim 1, wherein the first memory organizes data within a staging area that comprises, prior to the installing of the downloaded software in the second memory:
    a current folder containing a copy of existing software that is currently installed in the second memory; and
    a working folder containing the downloaded software.

3. The device of claim 2, wherein the operations further comprise, prior to the downloading of the software:
    receiving a digitally-signed manifest file from the external device that specifies a list of files included in the software update;
    determining that a first file in the list of files matches a second file of the copy of the existing software in the current folder;
    storing a copy of the second file in the working folder;
    performing a preliminary integrity check on the copy of the second file; and
    determining that the copy of the second file passed the preliminary integrity check;
    wherein the software downloaded from the external device excludes the first file, and
    wherein the performing of the first integrity check further comprises performing the first integrity check on the copy of the second file.

4. The device of claim 1, wherein the operations further comprise, after the installing of the downloaded software in the second memory:
    recording information that identifies hardware components that are currently installed in the device;
    powering off the device;
    powering on the device into a patient mode; and
    failing to detect, based on the information, that any of the hardware components have been replaced with a different hardware component.

5. A device comprising:
    a processor;
    first memory; and
    second memory storing computer-executable instructions that, when executed by the processor, cause performance of operations comprising:
        storing software received from an external device in the first memory as stored software, the stored software associated with a software update for the device;
        performing a first integrity check on the stored software;
        determining that the stored software passed the first integrity check;
        based on the stored software having passed the first integrity check, installing the stored software in the second memory as installed software;
        after the installing of the stored software, rebooting the device into a test mode; and
        performing a second integrity check on the installed software while the device is in the test mode.

6. The device of claim 5, wherein the operations further comprise:
determining that the installed software passed the second integrity check; and
enabling the device for use based on the installed software having passed the second integrity check.

7. The device of claim 6, wherein the device is a medical device, and wherein the enabling the device comprises enabling the medical device for use in association with a patient.

8. The device of claim 5, wherein the operations further comprise:
determining that the installed software did not pass the second integrity check; and
disabling the device so that the device is inoperable based on the installed software having not passed the second integrity check.

9. The device of claim 5, wherein the first memory organizes data within a staging area that comprises, prior to the installing of the stored software in the second memory:
a first folder containing a copy of existing software that is currently installed in the second memory; and
a second folder containing the stored software.

10. The device of claim 9, wherein the operations further comprise, prior to the storing of the software:
receiving a digitally-signed manifest file from the external device that specifies a list of files included in the software update;
determining that a first file in the list of files matches a second file of the copy of the existing software in the first folder;
storing a copy of the second file in the second folder;
performing a preliminary integrity check on the copy of the second file;
determining that the copy of the second file passed the preliminary integrity check; and
receiving, from the external device, the software excluding the first file,
wherein the performing of the first integrity check further comprises performing the first integrity check on the copy of the second file.

11. The device of claim 5, wherein the operations further comprise, after the installing of the stored software in the second memory:
recording information that identifies hardware components that are currently installed in the device;
powering off the device;
powering on the device;
detecting, based on the information, that a hardware component of the hardware components has been replaced with a different hardware component; and
disabling the device so that the device is temporarily unusable based on the detecting that the hardware component has been replaced.

12. A method comprising:
downloading software to first memory of a device as downloaded software, the downloaded software associated with a software update for the device;
performing, by the device, a first integrity check on the downloaded software;
determining, by the device, that the downloaded software passed the first integrity check;
based on the downloaded software having passed the first integrity check, installing the downloaded software in second memory of the device as installed software;
performing, by the device, a second integrity check on the installed software prior to enabling the device to execute the installed software to operate the device;
determining, by the device, that the installed software passed the second integrity check; and
after the determining that the installed software passed the second integrity check;
rebooting the device into a setup mode; and
sending, while the device is in the setup mode, information to a server computer indicating that the software update was successful.

13. The method of claim 12, further comprising, after the installing of the downloaded software, rebooting the device into a test mode, wherein the second integrity check is performed while the device is in the test mode.

14. The method of claim 12, further comprising:
enabling the device for use based on the installed software having passed the second integrity check.

15. The method of claim 12, further comprising, prior to the downloading of the software:
receiving, at the device, a digitally-signed manifest file that specifies a list of files included in the software update;
determining, by the device, that a first file in the list of files matches a second file of existing software that is currently installed on the device;
performing, by the device, a preliminary integrity check on a copy of the second file that is stored in the first memory; and
determining, by the device, that the copy of the second file passed the preliminary integrity check,
wherein the software downloaded to the first memory excludes the first file, and
wherein the performing of the first integrity check further comprises performing the first integrity check on the copy of the second file.

16. The method of claim 12, wherein the device is a medical device, and wherein the enabling the device comprises enabling the medical device to execute the installed software to operate the medical device in association with a patient.

17. The method of claim 12, wherein the information is first information, the method further comprising: after the installing of the downloaded software in the second memory:
recording second information that identifies hardware components that are currently installed in the device;
powering off the device;
powering on the device;
detecting, based on the second information, that a hardware component of the hardware components has been replaced with a different hardware component; and
disabling the device so that the device is temporarily unusable based on the detecting that the hardware component has been replaced.

18. The device of claim 1, wherein the device is a medical device.

19. The device of claim 18, wherein the medical device is an external defibrillator.

20. The device of claim 6, wherein the device is an external defibrillator, and wherein the enabling the device comprises enabling the external defibrillator for use in association with a patient.

* * * * *